US011471617B2

(12) United States Patent
Vonarburg et al.

(10) Patent No.: US 11,471,617 B2
(45) Date of Patent: Oct. 18, 2022

(54) NEBULTZATION OF IMMUNOGLOBULIN

(71) Applicants: CSL BEHRING AG, Bern (CH); PARI PHARMA GMBH, Starnberg (DE); MEDIZINISCHE HOCHSCHULE HANNOVER, Hannover (DE)

(72) Inventors: Cédric Pierre Vonarburg, Bern (CH); Karin Steinfuehrer, Germering (DE); Ulrich Baumann, Hannover (DE)

(73) Assignees: CSL BEHRING AG, Bern (CH); PARI PHARMA GMBH, Starnberg (DE); MEDIZINISCHE HOCHSCHULE HANNOVER, Hannover (DE)

( * ) Notice: Subject to any disclaimer, the term of this patent is extended or adjusted under 35 U.S.C. 154(b) by 1013 days.

(21) Appl. No.: 15/300,820

(22) PCT Filed: Apr. 2, 2015

(86) PCT No.: PCT/EP2015/057285
§ 371 (c)(1),
(2) Date: Sep. 30, 2016

(87) PCT Pub. No.: WO2015/150510
PCT Pub. Date: Oct. 8, 2015

(65) Prior Publication Data

US 2017/0021114 A1 Jan. 26, 2017

(30) Foreign Application Priority Data

Apr. 3, 2014 (EP) .................................... 14163399

(51) Int. Cl.
*A61M 11/00* (2006.01)
*A61K 9/00* (2006.01)
(Continued)

(52) U.S. Cl.
CPC ......... *A61M 11/001* (2014.02); *A61K 9/0078* (2013.01); *A61K 39/39591* (2013.01);
(Continued)

(58) Field of Classification Search
CPC .. A61M 11/001; A61M 11/005; A61M 15/00; A61M 15/0085; A61M 11/00;
(Continued)

(56) References Cited

U.S. PATENT DOCUMENTS 3,812,854 A * 5/1974 Michaels .......... A61M 15/0085 128/200.16
4,994,269 A 2/1991 Collins et al.
(Continued)

FOREIGN PATENT DOCUMENTS

EP 1 353 759 B1 1/2008
EP 1 927 373 B1 8/2012
(Continued)

OTHER PUBLICATIONS

Hertel et al., "Protein stability in pulmonary drug delivery via nebulization," Adv Drug Deliv Rev., 2015, 93: 79-94.
(Continued)

*Primary Examiner* — Valerie L Woodward
(74) *Attorney, Agent, or Firm* — Finnegan, Henderson, Farabow, Garrett & Dunner LLP

(57) ABSTRACT

The invention relates to methods for generating an aerosol by nebulization of a composition comprising polyclonal immunoglobulin (Ig). The selection of an efficient membrane nebulizer and a composition optimized for nebulization with such membrane nebulizer results in a particularly efficient method of generating an aerosol for administration of Ig to the respiratory tract.

15 Claims, 8 Drawing Sheets

(51) Int. Cl.

| | |
|---|---|
| ***A61K 39/395*** | (2006.01) |
| ***C07K 16/10*** | (2006.01) |
| ***C07K 16/12*** | (2006.01) |
| ***B05B 17/00*** | (2006.01) |
| ***A61M 15/00*** | (2006.01) |
| ***C07K 16/00*** | (2006.01) |
| ***A61K 39/00*** | (2006.01) |

(52) U.S. Cl.
CPC .......... *A61M 11/005* (2013.01); *A61M 15/00* (2013.01); *A61M 15/0085* (2013.01); *B05B 17/0646* (2013.01); *C07K 16/00* (2013.01); *C07K 16/1027* (2013.01); *C07K 16/1275* (2013.01); *A61K 2039/505* (2013.01)

(58) Field of Classification Search
CPC ............ A61K 9/0078; A61K 39/39591; A61K 47/183; A61K 2039/505; A61K 39/395; B05B 17/0646; C07K 16/00; C07K 16/1027; C07K 16/1275; A61P 11/00; A61P 37/02
See application file for complete search history.

(56) References Cited

U.S. PATENT DOCUMENTS

| | | | | |
|---|---|---|---|---|
| 6,983,747 | B2 † | 1/2006 | Gallem et al. | |
| 2002/0136695 | A1 * | 9/2002 | Simon .................. | A61K 9/0078 424/45 |
| 2004/0089295 | A1 * | 5/2004 | Gallem ............. | A61M 15/0085 128/203.12 |
| 2005/0147664 | A1 * | 7/2005 | Liversidge ............... | B82Y 5/00 424/452 |
| 2008/0128527 | A1 * | 6/2008 | Chan ................... | B05B 17/0623 239/4 |
| 2010/0260853 | A1 | 10/2010 | Basran et al. | |
| 2011/0236381 | A1 | 9/2011 | Garantziotis et al. | |
| 2012/0016818 | A1 | 1/2012 | Hackett et al. | |
| 2012/0308557 | A1 * | 12/2012 | Bolli .................... | A61K 9/0019 424/130.1 |
| 2013/0019860 | A1 * | 1/2013 | Depla .................. | A61K 9/0078 128/200.14 |
| 2013/0239956 | A1 | 9/2013 | Schulz et al. | |

FOREIGN PATENT DOCUMENTS

| | | | | |
|---|---|---|---|---|
| JP | 2011-506396 | A | | 3/2011 |
| WO | WO 92/01473 | A1 | | 2/1992 |
| WO | WO 95/03826 | | † | 2/1995 |
| WO | WO 2001/34232 | A1 | | 5/2001 |
| WO | WO 01/60420 | A1 | | 8/2001 |
| WO | WO 2002/064265 | A2 | | 8/2002 |
| WO | WO 2003/059424 | A1 | | 7/2003 |
| WO | WO 2004/004798 | A2 | | 1/2004 |
| WO | WO 2005/049078 | A2 | | 6/2005 |
| WO | WO 2006/122257 | A2 | | 11/2006 |
| WO | WO 2007/020073 | A1 | | 2/2007 |
| WO | WO 2008/102359 | A1 | | 8/2008 |
| WO | WO 2009/027095 | A1 | | 3/2009 |
| WO | WO 2010/066714 | A1 | | 6/2010 |
| WO | WO 2010/097119 | A1 | | 9/2010 |
| WO | WO 2011/095543 | A1 | | 8/2011 |
| WO | WO 2011/098552 | A2 | | 8/2011 |
| WO | WO 2011/134940 | A1 | | 11/2011 |
| WO | WO 2012/069531 | A2 | | 5/2012 |
| WO | WO 2012/168181 | | † | 12/2012 |
| WO | WO 2012/168181 | A1 | | 12/2012 |
| WO | WO 2013/132052 | A1 | | 9/2013 |

OTHER PUBLICATIONS

Schüle et al., "Sabilization of IgG1 in spray-dried powders for inhalation," Eur J Pharm Biopharm., 2008, 69:793-807.

Chan, et al., "Delivery of High Solubility Polyols by Vibrating Mesh Nebulizer to Enhance Mucociliary Clearance", Journal of Aerosol Medicine and Pulmonary Drug Delivery, 25(5):297-305 (2012).

Hertel et al., "That's cool!—Nebulization of thermolabile proteins with a cooled vibrating mesh nebulizer," Euro. J. Pharm. and Biopharm., 2014, 87:357-365.

Rimensberger et al., "Physical properties of aerosolized immunoglobulin for inhalation therapy," Journal of Aerosol Medicine, 8 (3): 255-262, (1995).

Lass et al., "New advances in aerosolized drug delivery: vibrating membrane nebulizer technology," Expert Opin. Drug Deliv., 3(5): 693-702, (2006).

Product Monograph, Sandoglobulin ® NF Liquid, Immune Globulin Intravenous (Human) 12% Solution for Infusion, CSL Behring Canada, Inc., Date of approval: Mar. 30, 2007.

Matthews et al., "Developing inhaled protein therapeutics for lung diseases," Mol Biomed., 2020, 1 (1):11.

Hong et al., "Viscosity control of protein solution by small solutes: a review," Curr Protein Pept Sci., 2018, 19(8):746-758.

Respaud et al., "Effect of formulation on the stability and aerosol performance of a nebulized antibody," MAbs, 2014;6(5):1347-1355.

Lintz et al., "Influence of Viscosity and Surface Tension on the Nebulization Efficiency of a Jet (LC PLUS®) and a Vibrating Membrane Type Nebulizer (e-Flow™)," AAPS Annual Meeting, Denver, Oct. 21-26, 2001, 1 page.

Vonarburg et al., "Topical application of nebulized human IgG, IgA and IgAM in the lungs of rats and non-human primates," RespirRes., 2019, 20(1):99, 16 pages.

Omron pamphlet—Micro A-I-R, "What is Ultrasonic Mesh Technology", (2 pages) (Translation—1 page).

Aeroneb Go Instruction Manual, 2009 evo Medical Solutions, (10 pages).

Renaud Respaud, et al., Expert Opinion on Drug Delivery, "Nebulization as a delivery method for mAbs in respiratory diseases" (14 pages) (2014).

Anand, V.K. (May 2004) "Epidemiology and economic impact of rhinosinusitis" *Ann Otol Rhinol Laryngol*, 113:3-5.

Council of Europe (Aug. 3, 20161) "Preparations for Nebulisation: Characterisation" in *European Pharmacopoeia* 9.0. The European Directorate forthe Quality of Medicines & Healthcare (edqm) [online], Retrieved from: http://online6.edam.eu/ep900/; 2.9.44, pp. 378-381.

Gregersen, S. et al. (Jun. 2010) "Development of pulmonary abnormalities in patients with common variable immunodeficiency: associations with clinical and immunologic factors" *Ann Allergy Asthma Immunol*, 104(6):503-510.

James, A.C. et al. (1991) "The Respiratory Tract Deposition Model Proposed by the ICRP Task Group" *Radiat Prot Dosimetry*, 38(1-3):159-165.

Khalid, A.N. et al. (May 2004) "Long-term quality of life measures after functional endoscopic sinus surgery" *Am J Rhinol*, 18(3):131-136.

Longet, S. et al. (Aug. 1, 2014) "Reconstituted Human Polyclonal Plasma-derived Secretory-like IgM and IgA Maintain the Barrier Function of Epithelial Cells Infected with an Enteropathogen" *J Biol Chem*, 289(31):21617-21626.

Oksenhendler, E. et al. (May 15, 2008) "Infections in 252 patients with common variable immunodeficiency" *Clin Infect Dis*, 46(10):1547-1554.

Quinti, I. et al. (Mar. 2, 2011) "Effectiveness of immunoglobulin replacement therapy on clinical outcome in patients with primary antibody deficiencies: Results from a multicenter prospective cohort study" *J Clin Immunol*, 31:315-322.

Rimensberger, P.C. and C. Roth (1995) "Physical Properties of Aerosolized Immunoglobulin for Inhalation Therapy" *Journal of Aerosol Medicine*, 8(3):255-262.

International Search Report and Written Opinion, including Notification of Transmittal, dated Jun. 29, 2015, in International Patent Application No. PCT/EP2015/057285, filed Apr. 2, 2015, by CSL Behring AG (11 pages).

(56) References Cited

OTHER PUBLICATIONS

Rimensberger et al., Physical properties of aerosolized immunoglobulin for inhalation therapy, Journal of aerosol medicine vol. 8, No. 3, 1995.†
Lass et al., new advances in aerosolized drug delivery: vibrating membrane nebulizer technology, 10.1517/17425247.3.5.693, 2006.†
Product Monograph, Sandoglobulin® NF Liquid, immune Globulin Intravenous (human) 12% solution for infusion, date of approval: Mar. 30, 2007.†

* cited by examiner
† cited by third party

NEBULTZATION OF IMMUNOGLOBULIN

This application is the United States national stage entry under 35 U.S.C. § 371 of International Application No. PCT/EP2015/057285, filed on Apr. 2, 2015 and published as WO 2015/150510 A1, which claims priority to European Patent Application No. 14163399.0, filed on Apr. 3, 2014. The contents of these applications are each incorporated herein by reference in their entirety.

FIELD OF THE INVENTION

The invention relates to a method of generating an aerosol for therapeutic purposes. More specifically, the invention relates to a method of nebulizing a composition containing immunoglobulin (Ig), in particular polyclonal immunoglobulins, such as immunoglobulin G (IgG), immunoglobulin A (IgA) or immunoglobulin M (IgM) or combinations thereof.

BACKGROUND OF THE INVENTION

Immunoglobulins (Ig) are components of human blood plasma which play an important role in immunological reactions. These specific immune proteins are synthesized by B-lymphocytes and found in blood plasma, lymph and other body secretions of all vertebrates. Immunoglobulins constitute approximately 20% of the plasma proteins in humans. Three immunoglobulin classes, IgG, IgA and IgM, are more important than the others. Human IgG represents the most abundant immunoglobulin in plasma, whereas IgA represents the main antibody class in external secretions such as saliva, tears and mucus of the respiratory and intestinal tracts. IgA forms one of the first lines of defense against bacterial and viral pathogens. IgM is by far the physically largest antibody in the human circulatory system, appears early in the course of an infection and usually reappears, to a lesser extent, after further exposure.

Over the last century, immunoglobulin preparations were successfully used for the treatment of infectious diseases, as replacement therapy in patients with primary immunodeficiency disorders and for the prophylaxis and treatment of various inflammatory and autoimmune conditions, as well as certain neurological disorders.

These immunoglobulin preparations were developed for systemic administration, and were largely comprised of IgG. Currently, these preparations are derived from pooled plasma of thousands of healthy donors (1,000 to 60,000 donors) and contain both specific and natural antibodies, reflecting the cumulative antigen experience of the donor population. This large spectrum of specific and natural antibodies can recognize a broad range of antigens (e.g. pathogens, foreign antigens and self/autoantigens).

Generally immunoglobulins are administered intravenously or subcutaneously. Several commercial formulations are available for these administration routes. Furthermore, topical administration of immunoglobulins, more specifically administration to the respiratory tract (including upper respiratory tract: nose and nasal passages, paranasal sinuses, throat, oropharynx, pharynx, voice box, larynx and trachea; as well as lower respiratory tract: respiratory airways, lungs, bifurcation, bronchi, and bronchioles, respiratory bronchioles, alveolar ducts, alveolar sacs, and alveoli) has been suggested.

For example, U.S. Pat. No. 4,994,269 describes a method for topical administration of antibodies to *P. aeruginosa*. The antibodies can be administered in the form of an aerosol, e.g. via application to the nose, as an aerosol to the lungs or via intratracheal administration.

WO 92/01473 describes a method which comprises administering into the lower respiratory tract of a susceptible host a small particle (<2 μm) aerosol of a mixture of specific monoclonal antibodies directed against the various protective antigenic sites present on a major protective viral surface antigen(s).

In Rimensberger and Roth ("Physical Properties of Aerosolized Immunoglobulin for Inhalation Therapy", Journal of Aerosol Medicine, Vol. 8(3), pp 255-262, 1995), the nebulization of an immunoglobulin solution (IVIG) was evaluated with four compressed air nebulizers.

US 2002/0136695 describes aerosol administration, by metered dose inhaler or nebulizer, of immunoglobulin A for the prevention or treatment of diseases including immunodeficiencies and infections.

WO 03/059424 describes a controller which can control an aerosol generator based upon the identity of the contents of a nebule having an identification marker/label. The system can be used for the nebulization of several drug groups. Antibodies are mentioned as one of the drug groups.

WO 2004/004798 describes methods and compositions for the systemic delivery of therapeutics by administering an aerosol containing antibodies or conjugates of a therapeutic agent with an FcRn binding partner to epithelium of central airways of the lung. The methods and products have the advantage of not requiring administration to the deep lung in order to effect systemic delivery. The use of aerosol generators with different working principles is suggested.

WO 2006/122257 describes methods and compositions employing an antibody that inhibits activation of the complement system and that can be used to prevent or treat a pulmonary disease or condition. Different nebulizer types are suggested for administration of monoclonal antibodies.

WO 2011/098552 describes methods for the preparation of an aerosol of immunoglobulin single variable domains wherein the amount of aggregate formation is significantly reduced.

Although these documents suggest several methods of applying different types of antibodies, there is still a need for a method of nebulizing polyclonal Ig, e.g. IgG, IgA, IgM, or combinations thereof, in a particularly fast and efficient manner.

Therefore, it is an object of the present invention to provide a method for generating an aerosol of a composition containing polyclonal Ig, e.g. IgG, IgA, IgM or combinations thereof, to deliver polyclonal Ig to the respiratory tract of a patient in an efficient manner, for example the delivered dose (DD) of the aerosol generator may be at least 40%, or preferred at least 50%, the respirable fraction (particle size below 5 μm MMD) should be at least 70% or preferred at least 80% and also the foaming characteristics and the residual volume of the inserted fluid in the liquid reservoir after aerosol generation may be reduced, for example below 1.0 mL or preferred below 0.5 mL, or more preferred below 0.3 mL.

SUMMARY OF THE INVENTION

The invention provides a method of generating an aerosol comprising the steps of (a) providing a liquid aqueous composition comprising a polyclonal Ig, e.g. IgG, IgA, IgM or combinations thereof, wherein the concentration of the Ig is in the range of 20 to 200 mg per mL; (b) providing a membrane nebulizer having a reservoir into which the composition is filled and (c) nebulizing the composition using the nebulizer to obtain an aerosol (aerosol generation).

In preferred embodiments, the Ig is polyclonal. Preferably, the Ig is polyclonal IgG, polyclonal monomeric IgA, polyclonal dimeric IgA, polyclonal IgM, or combinations thereof. In some embodiments the composition may additionally comprise secretory component, preferably recombinantly produced human secretory component.

In specific embodiments, the concentration of Ig, e.g. IgG, IgA, IgM or combinations thereof, in the liquid aqueous composition is in the range of 20 to 100 mg per mL. Furthermore, the composition can comprise a stabilizer. The stabilizer can be proline. Other excipients such as surfactants may also be contained in the composition.

In particular embodiments, the nebulizer reservoir is isolated from the atmosphere so that the pressure inside the reservoir decreases before or during step (c). In a preferred embodiment, the nebulizer is a vibrating membrane nebulizer. In certain embodiments, the nebulizer is specifically adapted for generating an aerosol targeting either the lower respiratory tract and/or the upper respiratory tract.

In one aspect, the method of the invention produces an aerosol containing at least 40%, preferably at least 50%, more preferably at least 60% of the dose of the Ig, e.g. IgG, IgA, IgM or combinations thereof, filled in the reservoir. In another aspect, the method produces an aerosol wherein the activity of the Ig, e.g. IgG, IgA, IgM or combinations thereof, is at least 60%, preferably at least 70%, more preferably at least 80%, even more preferably at least 90% of the activity in the composition filled in the reservoir.

Further embodiments of the invention will become obvious on the basis of the following detailed description, the examples and the claims.

DETAILED DESCRIPTION OF THE INVENTION

Figure 1:
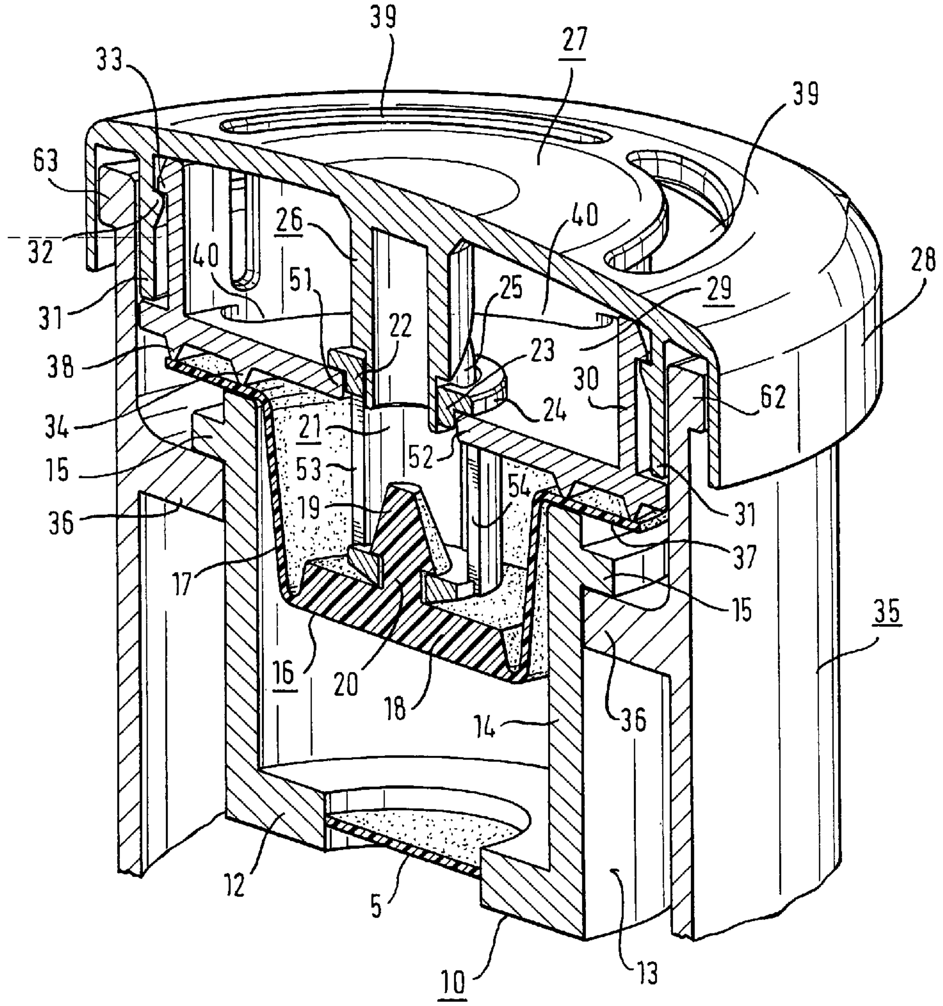
FIG. 1 shows a schematic representation of a known membrane nebulizer which can be used in the present invention.

The method of the invention is a method of generating an aerosol by nebulizing a liquid aqueous composition. Liquid aqueous compositions are liquid systems wherein the liquid carrier or solvent consists predominantly or completely of water. In specific cases, the liquid carrier can contain small fractions of one or more liquids which are at least partly miscible with water.

The composition comprises polyclonal immunoglobulin, which is typically obtained from plasma of human donors. Preferably, the plasma from multiple donors is pooled, for example from more than 100 donors, preferably from more than 500 donors, even more preferably from more than 1,000 donors. Typically the plasma pools are subjected to ethanol fractionation, followed by several purification steps, such as further precipitation steps and/or column chromatography steps, as well as steps to inactivate and remove viral and other pathogens such as nanofiltration or solvent/detergent treatment.

The composition comprises polyclonal immunoglobulin, which is also referred to as Ig. Such polyclonal Ig, for example IgG, IgA, IgM or combinations thereof, can be obtained from the plasma of human blood donors. Normal human IgG can be obtained with a purity of at least 95% IgG. Thus, in one embodiment, the IgG contained in the composition used in the method according to the invention generally has a purity of at least 95% IgG, preferably at least 96% IgG, more preferably at least 98% IgG, even more preferably at least 99% IgG. Preferably it contains only minor amounts of IgA. For example, in one embodiment the composition contains maximally 25 μg IgA per mL.

In another specific embodiment, the composition comprises IgA with a purity of at least 90%, preferably at least 92%, more preferably at least 94%, even more preferably at least 96%, most preferably at least 98%. Preferably, the IgA is purified from human plasma; however, other sources of IgA may also be used, such as milk, saliva, or other IgA-containing body fluids. In another specific embodiment, the IgA is monomeric IgA. In yet another specific embodiment, the IgA is enriched in dimeric IgA; preferably at least 20% of the IgA is in dimeric form, more preferably at least 30%, even more preferably at least 40%, most preferably at least 50%. Optionally, the IgA composition may additionally comprise secretory component, preferably recombinantly produced secretory component. For example compositions as disclosed in WO2013/132052, incorporated as reference in its entirety, may be used.

In yet another specific embodiment, the composition comprises IgM. In one embodiment, the composition comprises IgM and IgA. In a preferred embodiment the composition comprises IgM and dimeric IgA, which also comprises a J-chain. Optionally the composition may also comprise secretory component, preferably recombinantly produced secretory component. In yet another embodiment, the composition comprises IgM, IgA and IgG. In a specific embodiment, such a composition may contain 76% IgG, 12% IgA and 12% IgM.

In the method of the invention, relatively high concentrations of Ig, for example IgG, IgA, IgM, or combinations thereof, are used. More particularly, the concentration of Ig, especially IgG, IgA, IgM or combinations thereof, ranges between 20 and 200 mg/mL. Preferably, the concentration ranges between 20 and 190 mg/mL, 20 and 180 mg/mL, 20 and 170 mg/mL, 20 and 160 mg/mL, 20 and 150 mg/mL, 30 and 200 mg/mL, 30 and 190 mg/mL, 30 and 180 mg/mL, 30 and 170 mg/mL, 30 and 160 mg/mL, 30 and 150 mg/mL, 40 and 200 mg/mL, 40 and 190 mg/mL, 40 and 180 mg/mL, 40 and 170 mg/mL, 40 and 160 mg/mL, 40 and 150 mg/mL. More preferably, the concentration ranges between 20 and 140 mg/mL, 20 and 130 mg/mL, 20 and 120 mg/mL, 30 and 140 mg/mL, 30 and 130 mg/mL, 30 and 120 mg/mL, 40 and 140 mg/mL, 40 and 130 mg/mL, 40 and 120 mg/mL, 50 and 140 mg/mL, 50 and 130 mg/mL or 50 and 120 mg/mL, even more preferably, the concentration is about 50 mg/mL, 60 mg/mL, 70 mg/mL, 80 mg/mL, 90 mg/mL, 100 mg/mL, 110 mg/mL, or 120 mg/mL. Relatively high concentrations are important to enable low fill volumes and short nebulization times and, thus, insure therapeutic efficiency of the method.

A membrane nebulizer is used to generate the aerosol according to the method of the invention. A nebulizer is defined herein as a device which is capable of aerosolizing a liquid material into a dispersed liquid phase. An aerosol is defined herein as a system comprising a continuous gas phase and, dispersed therein, a discontinuous or dispersed phase of liquid particles.

The aerosol generator may have a liquid reservoir configured to hold an initial volume of fluid, e.g. containing Ig, IgG, IgA, IgM or combinations thereof, a membrane having openings, the liquid reservoir being in communication with the membrane to supply the liquid, e.g. by gravitational force, to one side of the membrane, the membrane being oscillatable to transport the liquid through the openings whereby the liquid is emitted in the form of an aerosol on the other side of the membrane.

The aerosol generator may have a membrane which generates liquid droplets from a liquid present on the one side and releases them as aerosol on the other side when a part of a wall of the fluid reservoir is vibrated, and a vibration-generating device, e.g. a piezoelectric element, which is connected to a part of a wall of the fluid reservoir such that the part of a wall of the fluid reservoir is vibrated (passive membrane nebulizer, type I).

The aerosol generator may have a membrane which generates liquid droplets from a liquid present on the one side and releases them as aerosol on the other side when a part of a wall of the fluid supply (e.g. tube) is vibrated, and a vibration-generating device, e.g. a piezoelectric element, which is connected to the fluid supply such that the fluid supply is vibrated (passive membrane nebulizer, type II).

The aerosol generator may have a membrane which generates liquid droplets from a liquid present on the one side and releases them as aerosol on the other side when the membrane is vibrated, and a vibration-generating device, e.g. a piezoelectric element, which is connected to the membrane such that the membrane is vibrated (active membrane nebulizer).

The dispersed phase essentially consists of liquid droplets. The droplets of the dispersed phase comprise polyclonal Ig, e.g. IgG, IgA, IgM or combinations thereof, in a liquid environment. The liquid environment is mainly an aqueous phase, with or without further excipients as described further below. It will be understood by the person skilled in the art, that the features and preferences with respect to the liquid composition, as disclosed herein, may also be applied to the dispersed phase of the aerosol generated therefrom and vice versa.

The continuous gas phase of the aerosol may be selected from any gas or mixture of gases which is pharmaceutically acceptable. For example, the gas may simply be air or compressed air, which is most common in inhalation therapy using nebulizers as aerosol generators. Alternatively, other gases and gas mixtures, such as air enriched with oxygen, carbon dioxide, or mixtures of nitrogen and oxygen may be used.

Two values can be determined experimentally and may be useful to describe the particle size or droplet size of the generated aerosol: the mass median diameter (MMD) and the mass median aerodynamic diameter (MMAD). The difference between the two values is that the MMAD is normalized to the density of water (equivalent aerodynamic).

The MMAD may be measured by an impactor, for example the Anderson Cascade Impactor (ACI) or the Next Generation Impactor (NGI). Alternatively laser diffraction methods may be used, for example the Malvern MasterSizer X™, to measure the MMD.

The dispersed phase of the aerosol generated by the method of the invention exhibits a particle size, e.g. the MMD of preferably less than 10 μm, preferably from about 1 to about 6 μm, more preferably from about 1.5 to about 5 μm and even more preferably from about 2 to about 4.5 μm. Alternatively the particle size may have a MMAD of preferably less than 10 μm, preferably from about 1 to about 6 μm, more preferably from about 1.5 to about 5 μm and even more preferably from about 2 to about 4.5 μm. Another parameter describing the dispersed phase of the aerosol is the particle size distribution of the aerosolized liquid particles or droplets. The geometric standard deviation (GSD) is an often used measure for the broadness of the particle or droplet size distribution of generated aerosol particles or droplets.

The selection of the precise MMD within the above described range should take the target region or tissue for deposition of the aerosol into account. For example, the optimal droplet diameter will differ depending on whether oral, nasal or tracheal inhalation is intended, and whether upper and/or lower respiratory tract delivery (e.g. to the oropharynx, throat, trachea, bronchi, alveoli, lungs, nose, and/or paranasal sinuses) is focused upon. Additionally, the age dependent anatomic geometry (e.g. the nose, mouth or respiratory airway geometry) as well as the respiratory disease and condition of the patients and their breathing pattern belong to the important factors determining the optimal particle size (e.g. MMD and GSD) for drug delivery to the lower or upper respiratory tract.

Generally, small airways, which are defined by an internal diameter lower than 2 mm, represent almost 99% of the lung volume and therefore play an important role in lung function. Alveoli are sites in the deep lungs where oxygen and carbon dioxide are exchanged with the blood. Inflammation in the alveoli induced by some viruses or bacteria leads to fluid secretion on site and directly affects oxygen uptake by the lungs. Therapeutic targeting of deep pulmonary airways with aerosols requires aerosols having an MMD below 5.0 μm, preferably below 4.0 μm, more preferably below 3.5 μm and even more preferably below 3.0 μm.

For aerosol delivery to the respiratory tract, the aerosol has an MMD below 10.0 μm, preferably below 5.0 μm, more preferably below 3.3 μm, and even more preferably below 2.0 μm. Preferably, the MMD is (droplet sizes are) in the range from about 1.0 to about 5.0 μm and the size distribution has a GSD less than 2.2, preferably less than 2.0, more preferably less than 1.8 or even more preferably less than 1.6. Such particle size and particle size distribution parameters are particularly useful to achieve a high local drug concentration in the respiratory tract (e.g. lungs) of humans, including the bronchi and bronchioli, relative to the amount of drug which is aerosolized. In this context it must be considered that deep lung deposition requires smaller MMD's than deposition in the central airways of adults and children and for infants and babies even smaller droplet sizes (MMD's) in the range from about 1.0 to about 3.3 μm are more preferred and the range below 2.0 μm is even more preferred. Thus, in aerosol therapy it is common to evaluate the fraction of droplets smaller than 5 μm (representing the fraction that is respirable by an adult) and smaller than 3.3 μm (representing the fraction that is respirable by a child or is deposited in the deeper lungs of an adult). Also, the fraction of droplets smaller than 2 μm is often evaluated as it represents the fraction of the aerosol that could optimally reach terminal bronchioles and alveoli of adults and children and can penetrate the lungs of infants and babies.

In the method of the invention, the fraction of droplets having a particle size smaller than 5 μm is preferably greater than 65%, more preferably greater than 70% and even more preferably greater than 80%. The fraction of droplets having a particle size smaller than 3.3 μm is preferably greater than 25%, more preferably greater than 30%, even more preferably greater than 35% and still more preferably greater than 40%. The fraction of droplets having a particle size smaller than 2 μm is preferably greater than 4%, more preferably greater than 6% and even more preferably greater than 8%.

The aerosol can also be characterized by its delivered dose (DD) as determined in breath simulation experiments. The delivered dose can be used to calculate the respirable dose (RD), e.g. on the basis of the respirable fraction (RF) measured by laser diffraction (e.g. Malvern MasterSizer X™) or using an impactor (e.g. Anderson Cascade Impactor—ACI, or Next Generation Impactor—NGI). When applying the method of the invention in a breath simulation experiment (e.g. using a breathing simulator like BRS3000 from Copley or Compass II™ from PARI) with an adult breathing pattern (sinusoidal flow, 500 mL tidal volume, 15 breaths/min), and filling 2 mL of composition (e.g. 200 mg Ig, 200 mg IgG, 200 mg IgA, 200 mg IgM or combinations thereof) into the membrane nebulizer, the delivered dose (DD) is preferably higher than 40% (80 mg Ig, e.g. IgG, IgA, IgM or combinations thereof), more preferably higher than 45% (90 mg Ig, e.g. IgG, IgA, IgM or combinations thereof) and even more preferably higher than 50% (100 mg Ig, e.g. IgG, IgA, IgM or combinations thereof).

For the treatment of the upper airways, in particular the nose, nasal and/or sinonasal mucosa, osteomeatal complex, and paranasal cavities, an MMD below about 5.0 μm, or below about 4.5 μm, or below about 4.0 μm, or below about 3.3 or below about 3.0 μm is particularly suitable.

The suitability of the generated aerosol for application to the upper airways can be evaluated in nasal inhalation models such as the human nasal cast model described in WO 2009/027095. For aerosol delivery to the nose, e.g. the Sinus™ device (jet nebulizer) from PARI and also a membrane nebulizer (prototypes of Vibrent™ technology) exist.

The nebulizer used in the method of the invention is a membrane nebulizer. Preferably, the membrane nebulizer is a vibrating membrane nebulizer. Nebulizers of the latter type comprise a reservoir in which the liquid for the nebulization is filled. When operating the nebulizer, the liquid is fed to a membrane that is made to oscillate, i.e. vibrate (e.g. by means of a piezoelectric element). The liquid present at one side of the vibrating membrane is hereby transported through openings in the vibrating membrane (also referred to as "pores" or "holes") and takes the form of an aerosol on the other side of the vibrating membrane. (e.g. eFlow rapid and eRapid from PARI, HL100 from Health and Life as well as AeronebGo and AeronebSolo from Aerogen). Such nebulizers may be referred to as "active membrane nebulizers".

In other useful membrane nebulizers, the composition can be nebulized by vibrating the liquid rather than the membrane. Such an oscillating fluid membrane nebulizer comprises a reservoir in which the liquid to be nebulized is filled. When operating the nebulizer, the liquid is fed to a membrane via a liquid feed system that is made to oscillate (i.e. vibrate, e.g. by means of a piezoelectric element). This liquid feed system could be the vibrating back wall of the reservoir (e.g. AerovectRx™ Technology, Pfeifer Technology) or a vibrating liquid transporting slider (e.g. I-Neb™ device from Respironics, or U22™ device from Omron). These nebulizers may be referred to as "passive membrane nebulizers".

Different membrane types are available for the nebulization of liquids with a membrane nebulizer. These membranes are characterized by different pore sizes which generate aerosols with different droplet sizes (MMD's and GSD's). Depending on the characteristics of the composition and the desired aerosol characteristics, different membrane types (i.e. different modified membrane nebulizers or aerosol generators) can be used. In the method of the invention, it is preferred to use membrane types which generate an aerosol with an MMD in the range of 2.0 μm to 5.0, preferably in the range of 3.0 μm to 4.9 and more preferably in the range of 3.4 μm to 4.5 μm. In another embodiment of the invention, it is preferred to use membrane types built in aerosol generator devices which generate an aerosol, e.g. isotonic saline (NaCl 0.9%), with an MMD in the range of 2.8 μm to 5.5 μm, preferably in the range of 3.3 μm to 5.0 μm, and more preferably in the range 3.3 μm to 4.4 μm. In another embodiment of the invention, it is preferred to use membrane types built in aerosol generator devices which generate an aerosol, e.g. isotonic saline, with an MMD in the range of 2.8 μm to 5.5 μm, preferably in the range of 2.9 μm to 5.0 μm and more preferably in the range of 3.8 μm to 5.0 μm.

The inventors have found that the method of the invention functions particularly well when the reservoir is isolated from the atmosphere so that the pressure in the reservoir decreases before or during the step of nebulizing the liquid aqueous composition comprising the polyclonal Ig, for example IgG, IgA, IgM or combinations thereof (i.e. step (c)). In other words, the method is particularly effective if the liquid aqueous composition is fed to the membrane under a pressure which is slightly below the ambient pressure of the area into which the aerosol droplets are emitted. The initial pressure in the reservoir, before the step of nebulizing the liquid, is preferred at least 50 mbar, more preferred at least 75 mbar, and most preferred at least 100 mbar.

Moreover, the aerosol generator has a negative pressure generating device cooperating with the liquid reservoir so to increase the volume (V1) of the liquid reservoir in the sealed state of the liquid reservoir to volume (V2) before the membrane is oscillated (that is before starting administration or use). Such a negative pressure generating device may be formed as disclosed in U.S. Pat. No. 6,983,747 B2, which is incorporated by reference in its entirety. Alternatively, the negative pressure generating device may as well be configured as disclosed in WO 2007/020073 A1, which is incorporated by reference in its entirety.

To realize a decrease of pressure in the reservoir, it is particularly preferred to isolate the reservoir from the atmosphere by a sealing element (16) arranged on an opening in the reservoir (10) to provide a gas-tight seal for the opening, and a slidable element (21) connected to the sealing element (16) in such a way that a movement of the slidable element (21) effects a movement of at least one section (18) of the sealing element (16) whereby a negative pressure is generated in the reservoir (10), as shown in FIG. 1. Such method of decreasing the pressure inside the reservoir is described in WO 02/064265, which is incorporated by reference in its entirety. Alternatively, the negative pressure generating device may also be configured as disclosed in EP 1353759 B1, which is incorporated by reference in its entirety. In other useful membrane nebulizers, the negative pressure is generated in the sealed liquid reservoir by means of a closing element or mechanical system, e.g. using a volume expansion bellows, movement, sucking, pumping, or the like.

Alternatively, the negative pressure generating device in the reservoir may also be configured to generate a nearly constant negative pressure range in the reservoir during the complete aerosol generation process from the fluid or liquid. The negative pressure range in the reservoir, during the step of nebulizing the liquid, is preferred in the range of 50 to 400 mbar, more preferred in the range of 100 to 400 mbar, even more preferred in the range of 100 to 350 mbar, and most preferred in the range of 100 to 200 mbar. Such a negative pressure range device may be formed as disclosed in WO 2012/069531 A2, which is incorporated by reference in its entirety.

However, the negative pressure can also be generated during nebulization alone or the negative pressure generated by the closing element as described above can be maintained on a fairly constant level while carrying out the nebulization (i.e. step (c)).

If the method is intended for targeting the lower respiratory tract such as the bronchi or the deep lungs, it is particularly preferred that a piezoelectric perforated membrane-type nebulizer is selected for generating the aerosol. Examples of suitable nebulizers include the passive membrane nebulizer, such as I-Neb™, U22™, U1™, Micro Air™, the ultrasonic nebulizer, for example Multisonic™, and/or active membrane nebulizer, such as HL100™, Respimate™, eFlow™ Technology nebulizers, AeroNeb™, AeroNeb Pro™, AeronebGo™, and AeroDose™ device families as well as the prototype Pfeifer, Chrysalis (Philip Morris) or AerovectRx™ devices. A particularly preferred nebulizer for targeting the drug to the lower respiratory tract is a vibrating perforated membrane nebulizer or so called active membrane nebulizer, such as for example the eFlow™ nebulizer (electronic vibrating membrane nebulizer available from PARI, Germany). Alternatively a passive membrane nebulizer may be used, for example U22™ or U1™ from Omron or a nebulizer based on the Telemaq.fr technique or the Ing. Erich Pfeiffer GmbH technique.

A preferred membrane nebulizer for targeting the upper respiratory tract is a nebulizer which generates the aerosol via a perforated vibrating membrane principle, such as a modified investigational membrane nebulizer using the eFlow™ technology, but which is also capable of emitting a pulsating air flow so that the generated aerosol cloud pulsates (i.e. undergoes fluctuations in pressure) at the desired location or during transporting the aerosol cloud to the desired location (e.g. sinonasal or paranasal sinuses). This type of nebulizer has a nose piece for directing the flow transporting the aerosol cloud into the nose. Aerosols delivered by such a modified electronic nebulizer can reach sinonasal or paranasal cavities much better than when the aerosol is delivered in a continuous (non-pulsating) mode. The pulsating pressure waves achieve a more intensive ventilation of the sinuses so that a concomitantly applied aerosol is better distributed and deposited in these cavities.

More particularly, a preferred nebulizer for targeting the upper respiratory tract of a patient is a nebulizer adapted for generating an aerosol at an effective flow rate of less than about 5 liters/min and for simultaneously operating means for effecting a pressure pulsation of the aerosol at a frequency in the range from about 10 to about 90 Hz, wherein the effective flow rate is the flow rate of the aerosol as it enters the respiratory system of the patient. Examples of such electronic nebulization devices are disclosed in WO 2009/027095.

In a preferred embodiment of the invention, the nebulizer for targeting the upper respiratory tract is a nebulizer which uses a transportation flow that can be interrupted when the aerosol cloud reaches the desired location and then starts the pulsation of the aerosol cloud, e.g. in an alternating mode. The details are described in WO 2010/097119 A1 and WO 2011/134940 A1.

Whether adapted for pulmonary or sinonasal delivery, the nebulizer should preferably be selected or adapted to be capable of aerosolizing a unit dose at a preferred output rate. A unit dose is defined herein as a volume of the liquid aqueous composition comprising the effective amount of active compound, i.e. Ig, IgG, IgA, IgM or combinations thereof, designated to be administered during a single administration. Preferably, the nebulizer can deliver such a unit dose at a rate of at least 0.1 mL/min or, assuming that the relative density of the composition will normally be around 1, at a rate of at least 100 mg/min. More preferably, the nebulizer is capable of generating an output rate of at least 0.4 mL/min or 400 mg/min, respectively. In further embodiments, the liquid output rates of the nebulizer or the aerosol generator are at least 0.50 mL/min, preferably at least 0.55 mL/min, more preferably at least 0.60 mL/min, even more preferably at least 0.65 mL/min, and most preferably at least 0.7 mL/min, such devices called aerosol generator with a high output or high output rate. Preferably, the liquid output rate ranges between about 0.35 and about 1.0 mL/min or between about 350 and about 1000 mg/min; preferably the liquid output rate ranges between about 0.5 and about 0.90 mL/min or between about 500 and about 800 mg/min. Liquid output rate means the amount of liquid composition nebulized per time unit. The liquid may comprise an active compound, drug, Ig, IgG, IgA, IgM or combinations thereof and/or a surrogate such as sodium chloride 0.9%.

Figure 2:
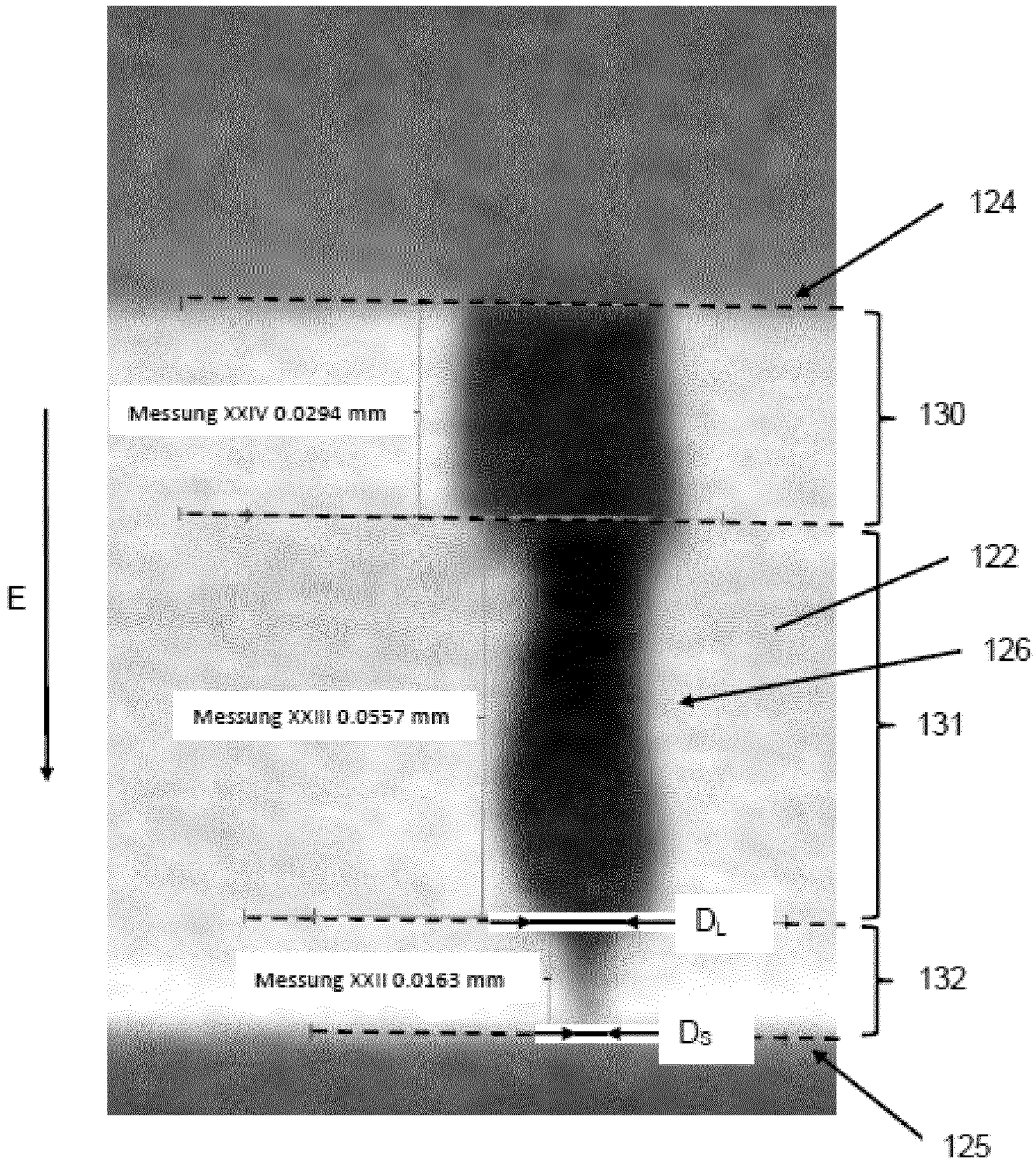
FIG. 2 shows a computer tomography (CT) picture of a known membrane which can be used in the present invention.

It has been found that for the method of the invention, i.e. for the generation of an aerosol from a polyclonal Ig, e.g. IgG, IgA, IgM or combinations thereof, composition in a concentration of 20 to 200 mg per mL, specific membrane types can be used in the nebulizer to increase the output rate. For example, it has been found to be particularly advantageous with respect to output rate to use a membrane (122) having a first side (124) for being in contact with the fluid and an opposite second side (125), the membrane having a plurality of through holes (126) penetrating the membrane in an extension direction (E) from the first side to the second side, whereby the fluid passes the through holes from the first side to the second side when the membrane is vibrated for generating the aerosol at the second side, each through hole (126) having along its extension direction (E) a smallest diameter ($D_S$), a larger diameter ($D_L$) that is larger than the smallest diameter and defined by that diameter that is closest to triple, preferably twice said smallest diameter, each through hole having a nozzle portion (132) defined by that continuous portion of the through hole in the extension direction comprising the smallest diameter of the through hole and bordered by the larger diameter of the through hole, characterized in that the ratio of the total length of each through hole (126) in the extension direction to the length of a respective one of said nozzle portions (132) in the extension direction is at least 4. Such a membrane is described in WO 2012/168181 A1 and shown in FIG. 2, which shows a computer tomography (CT) picture with included description.

The output rate of the nebulizer should be selected to achieve a short nebulization time of the liquid composition. Obviously, the nebulization time will depend on the volume of the composition which is to be aerosolized and on the output rate. Preferably, the nebulizer should be selected or adapted to be capable of aerosolizing a volume of the liquid composition comprising an effective dose of polyclonal Ig, e.g. IgG, IgA, IgM or combinations thereof, within not more than 20 minutes. More preferably, the nebulization time for a unit dose is not more than 15 minutes. In a further embodiment, the nebulizer is selected or adapted to enable a nebulization time per unit dose of not more than 10 minutes, and more preferably not more than 6 minutes and even more preferably not more than 3 minutes. Presently most preferred is a nebulization time in the range from 0.5 to 5 minutes.

The volume of the composition that is nebulized in step (c) of the method according to the invention is preferably low in order to allow short nebulization times. The volume, also referred to as the volume of a dose, or a dose unit volume, or a unit dose volume, should be understood as the volume which is intended for being used for one single administration or nebulizer therapy session. Specifically, the volume may be in the range from 0.3 mL to 6.0 mL, preferably 0.5 mL to 4.0 mL, or more preferably 1.0 mL to about 3.0 mL, or even more preferably about 2 mL. In case a residual volume is desired or helpful, this residual volume should be less than 1.0 mL, more preferably less than 0.5 mL, and most preferably less than 0.3 mL. The effectively nebulized volume is then preferably in the range from 0.2 to 3.0 mL or 0.5 to 2.5 mL, or more preferably in the range from 0.75 to 2.5 mL or 1.0 to 2.5 mL.

Preferably, the nebulizer is adapted to generate an aerosol where a major fraction of the loaded dose of liquid composition is delivered as aerosol, i.e. to have a high output. More specifically, the nebulizer is adapted to generate an aerosol which contains at least 50% of the dose of the Ig, e.g. IgG, IgA, IgM or combinations thereof, in the composition, or, in other words, which emits at least 50% of the liquid composition filled in the reservoir. Especially in comparison with monoclonal antibodies, of which the doses do not need to be as high due to their specificity, it is important to select a nebulizer which can generate such high output of polyclonal Ig, e.g. IgG, IgA, IgM or combinations thereof. It was found that a membrane nebulizer as used in the method of the invention is capable of generating an aerosol of a polyclonal Ig, e.g. IgG, IgA, IgM or combinations thereof, composition with a particularly high output.

Furthermore, the nebulizer can comprise a chamber with an inhalation and exhalation valve, also referred to as aerosol chamber or mixing chamber. The membrane nebulizer reservoir is filled with liquid and the membrane generates the aerosol into the mixing chamber. Preferably the exhalation valve is located near the mouth piece and the inhalation valve is located near the incoming ambient air opening. This reduces loss of aerosol during the exhalation phase of a patient, since the aerosol that is produced during that phase is largely maintained in the mixing chamber until the patient inhales. A membrane nebulizer with such a mixing chamber is described in WO 2001/34232 and WO 2010/066714. Differently sized mixing chambers can be used. In the method of the invention, it is preferred to use a large mixing chamber having a volume of at least 45 mL, more preferably at least 50 mL, and even more preferably at least 60 mL. Alternatively a large mixing chamber having a volume in the range of 60 to 150 mL may be used. A membrane nebulizer with such a large mixing chamber is described in EP 1 927 373, which is incorporated by reference in its entirety.

Preferably, the liquid aqueous composition used in the method of the invention contains one or more stabilizers. A commonly encountered issue when formulating liquid immunoglobulin formulations is that the immunoglobulins tend to aggregate and form precipitates if not sufficiently stabilized with appropriate additives. Several amino acids, such as proline, glycine and histidine, or saccharides, or sugar alcohols, or proteins, such as albumin, or combinations thereof, are known to stabilize immunoglobulins in liquid formulations and can be used in the liquid aqueous composition.

For pulmonary administration of Ig, e.g. IgG, IgA, IgM or combinations thereof, by nebulization it is preferred to use high concentrations of Ig, e.g. IgG, IgA, IgM or combinations thereof. Generally, high doses of polyclonal Ig are required, but it is important to minimize the volume to be nebulized as much as possible in order to keep the nebulization time as short as possible. The latter is relevant with respect to patient compliance. Thus, Ig compositions having a high Ig concentration are preferred in the method of the invention. However, it was found that an increase of the Ig concentration results in a non-linear increase of viscosity.

It is generally known that the dynamic viscosity of a liquid composition has an influence on the droplet size distribution of the aerosol formed by nebulization of that composition and on the efficiency of nebulization. For nebulization of liquid compositions with a membrane nebulizer, it is generally preferred that the liquid composition used in the method of the invention exhibits a dynamic viscosity in the range from about 0.8 to about 4.0 mPa·s at a temperature of 20° C.+/−0.1° C.). More preferably, the dynamic viscosity is in the range of about 1.0 to about 3.5 mPa·s at a temperature of 20° C.+/−0.1° C. when measured with a falling ball viscosimeter ("Kugelfallviskosimeter") according to Höppler in accordance with the European Pharmacopoeia Version 6.0 at 2.2.49 and the requirements of DIN 53015. Thereby, the rolling time of a ball or sphere in a tube or capillary of defined dimensions and having a defined slope is determined. Based on the rolling time, the viscosity of the liquid in the tube or capillary can be determined. The measurements are typically made at a temperature of 20.0° C.+/−0.1° C.

One embodiment of the invention is a method for generating an aerosol of an immunoglobulin solution, wherein the immunoglobulin solution has a viscosity of 1 to 17 mPa s, 1 to 16 mPa s, 1 to 15 mPa s, 1 to 14 mPa s, 1 to 13 mPa s, 1 to 12 mPa s, 1 to 11 mPa s, 1 to 10 mPa s, 2 to 17 mPa s, 2 to 16 mPa s, 2 to 15 mPa s, 2 to 14 mPa s, 2 to 13 mPa s, 2 to 12 mPa s, 2 to 11 mPa s, 2 to 10 mPa s, 3 to 17 mPa s, 3 to 16 mPa s, 3 to 15 mPa s, 3 to 14 mPa s, 3 to 13 mPa s, 3 to 12 mPa s, 3 to 11 mPa s, 3 to 10 mPa s; preferably the immunoglobulin solution has a viscosity of 1 to 9 mPa s, 1 to 8 mPa s, 1 to 7 mPa s, 1 to 6 mPa s, 2 to 9 mPa s, 2 to 8 mPa s, 2 to 7 mPa s, 2 to 6 mPa s, 3 to 9 mPa s, 3 to 8 mPa s, 3 to 7 mPa s, or 3 to 6 mPa s; more preferably the immunoglobulin solution has a viscosity of 1 to 5 mPa s, 1 to 4 mPa s, 2 to 5 mPa s, 2 to 4 mPa s, 3 to 5 mPa s, or 3 to 4 mPa s.

To avoid nebulization issues caused by high viscosity, it has been found that proline is preferably used as a stabilizer, since a relatively low viscosity of an Ig, e.g. IgG, IgA, IgM or combinations thereof, preparation can be achieved even if the concentration of Ig is high, as disclosed in WO2011/095543. Thus, it has been found that it is particularly advantageous to add proline to polyclonal Ig compositions when these compositions are intended for use in methods of generating an aerosol with a nebulizer. Proline provides on the one hand the desired stability of Ig in a liquid composition, and on the other hand it reduces the viscosity of the composition, thus allowing the nebulization of a small liquid volume with a high Ig concentration, which results in a fast and efficacious treatment by nebulization.

When using proline as a stabilizing agent, it is particularly preferred to use L-proline. L-proline is normally present in the human body and has a very favorable toxicity profile. The safety of L-proline was investigated in repeated-dose toxicity studies, reproduction toxicity studies, mutagenicity studies and safety pharmacology studies, and no adverse effects were noted.

Generally, the amount of proline, and more preferably of L-proline, added to the composition is such that the concentration of proline in the immunoglobulin composition ranges from about 10 to about 1000 mmol/L, more preferably from about 100 to about 500 mmol/L, and most preferably is about 250 mmol/L.

In one embodiment of the invention, the viscosity of liquid aqueous composition comprising polyclonal IgG and a stabilizing amount of proline ranges between 1 mPa·s and 17 mPa·s (at a temperature of 20.0° C.+/−0.1° C.). The viscosity of a composition comprising 100 mg/mL polyclonal IgG and 250 mM proline is about 3 mPa·s at a temperature of 20.0° C.+/−0.1° C.

An IgG composition used according to the invention and containing proline has a pH of 4.2 to 5.4, preferably 4.6 to 5.0, most preferably about 4.8, which further contributes to the high stability of the preparation.

The use of proline allows preparing a composition where stability of the formulation is increased and viscosity of the composition is reduced by using one single agent. This results in a composition which is particularly useful in methods for generating an aerosol with a membrane nebulizer.

The liquid composition used in the method of the invention can also comprise further pharmaceutically acceptable excipients, which serve to optimize the characteristics of the composition and/or the characteristics of the aerosol. Examples of such excipients are excipients for adjusting or buffering the pH, excipients for adjusting osmolality, antioxidants, surfactants, excipients for sustained release or prolonged local retention, taste-masking agents, sweeteners, and flavors. These excipients are used to obtain an optimal pH, osmolality, viscosity, surface tension and taste, which support the formulation stability, the aerosolization, the tolerability and/or the efficacy of the formulation upon inhalation.

The immunoglobulin solutions used in the invention have a surface tension of about 60 to 75 mN/m, preferably about 64 to 71 mN/m.

For example, surfactants can be added to the composition. These can help to control the rate of aggregation of immunoglobulins in the composition (i.e. during storage and in the reservoir) and during nebulization (i.e. during and after passing the membrane of the nebulizer), thereby having an influence on the activity of the Ig, e.g. IgG, IgA, IgM or combinations thereof, in the aerosol. Examples of useful surfactants are polysorbates, such as polysorbate 80.

Generally, it was found that applying the method of the invention results in an aerosol in which the activity of the Ig, e.g. IgG, IgA, IgM or combinations thereof, is at least 80% of the activity of the Ig in the composition filled into the nebulizer reservoir. Thus, the method of the invention neither results in significant aggregation of the Ig, nor in significant denaturation of the Ig. The activity of Ig can be determined by standard immunological methods (e.g. ELISA, flow cytometry and cell-based assays).

The aerosol generated by the method of the invention can be used for therapy and prevention of several conditions where polyclonal Ig, e.g. IgG, IgA, IgM or combinations thereof, is indicated.

In particular, the aerosol generated by the method of the invention can be used in patients who are in need of replacement therapy, i.e. in patients having a lung disease, sinusitis, patients at risk of recurrent infections because they do not have sufficient antibodies, or, in other words, who have an immunodeficiency syndrome. More specifically, the aerosol can be used in the treatment of patients with primary immunodeficiency (PID), secondary immunodeficiency (SID), such as hypogammaglobulinemia and recurrent bacterial infections due to chronic lymphoid leukemia or multiple myeloma, hypogammaglobulinemia after allogeneic blood-stem-cell transplantation (HSCT), hypogammaglobulinemia due to chemotherapy for treatment of malignancies, hypogammaglobulinemia due to treatment with biologicals, e.g. rituximab, for treatment of malignancies or autoimmune diseases, susceptibility to airway infections due to immunosuppressive drugs for treatment of autoimmune disease or solid organ transplantation, and patients having acquired immune deficiency syndrome (AIDS, HIV). In addition, the aerosol can be used in treatment of conditions with chronic airway infections, such as cystic fibrosis and primary ciliar dyskinesia, chronic obstructive pulmonary disease (COPD), chronic bacterial sinusitis, in conditions with chronic inflammation of the airways, such as bronchiolitis obliterans, bronchiolitis obliterans organizing pneumonia, non-cystic fibrosis bronchiectasis, chronic bacterial bronchitis, interstitial lung disease, bronchial asthma, or usual interstitial pneumonia, or in allergic conditions such as exogenous allergic alveolitis, allergic asthma, or chronic sinusitis.

Furthermore, the aerosol generated by the method of the invention can be used for immunomodulation in patients having an abnormal immune system that needs to be adjusted. Thus, the aerosol can be used in patients with idiopathic (or primary) thrombocytopenic purpura (ITP) who are at high risk of bleeding or who need correction of the number of thrombocytes before operations, in patients with Guillain-Barré syndrome, Kawasaki disease or chronic inflammatory demyelinating polyneuropathy (CIDP).

The commercially available immunoglobulin formulations listed in the following table can be used in the method of the invention as the liquid aqueous composition comprising a polyclonal immunoglobulin G:

| Name | Form | IgG content (%) | Available IgG concentration (%) | Osmolality | Stabilizer | pH |
|---|---|---|---|---|---|---|
| Bivigam™ | liquid | ≥96 | 10 | NR** | Glycine, PS80* | 4.0-4.6 |
| Clairyg ™ | liquid | ≥95 | 5 | NR** | Mannitol, Glycine, PS80* | NR** |
| Flebogam ™ 5% | liquid | ≥97 | 5 | 192-1074 mOsmol/L | 5% D-Sorbitol | 5.0-6.0 |
| Flebogammadit™ 5% | liquid | ≥97 | 5 | 240-350 mOsmol/L | 5% D-Sorbitol | 5.0-6.0 |
| Gammagard™ Liquid 10% | liquid | ≥98 | 10 | 240-300 mOsmol/kg | Glycine | 4.6-5.1 |
| Gammaplex ™ | liquid | ≥95 | 5 | 420-500 mOsmol/kg | Glycine, sorbitol, PS80* | 4.8-5.1 |
| Gammunex ™ 10% | liquid | ≥98 | 10 | 258 mOsmol/kg | Glycine | 4.0-4.5 |
| IG Vena™ N | liquid | ≥98 | 10 | NR** | Maltose | NR** |
| Intratecth ™ | liquid | ≥96 | 5 | 300 mOsmol/kg | Glycine | NR** |
| Kiovig™ | liquid | ≥98 | 10 | NR** | Glycine | 4.6-5.1 |
| Nanogam™ | liquid | ≥95 | 5 | NR** | Glucose | NR** |
| Octagam ™ | liquid | ≥96 | 5 | 310-380 mOsmol/kg | Maltose | 4.5-5.0 |
| Octagam ™ 10% | liquid | ≥95 | 10 | ≥240 mOsmol/kg | Maltose | 5.1-6.0 |
| Polyglobin™ N10% | liquid | ≥98 | 10 | NR** | Glycine | NR** |
| Sandoglobulin™ NF liquid | liquid | ≥96 | 12 | NR** | L-isoleucine and L-proline | NR** |
| Vigam™ | liquid | ≥95 | 5 | NR** | Sucrose | 4.8-5.1 |

*PS80 = Polysorbate 80
**NR = Not reported

EXAMPLES

The following non-limiting examples serve to illustrate the invention.

Example 1

Nebulization of IgG

The nebulization of a composition containing 100 mg/mL normal human immunoglobulin and 0.25 mol/L proline in water for injection was evaluated. The immunoglobulin fraction contained at least 98% of IgG and the composition contained at most 25 μg of IgA per mL; it was prepared from the plasma of human blood donors. The composition had a pH of 4.82, a density of 1.0336 g/mL, a viscosity of 3.33 mPa·s at 20° C., a surface tension of 71.1 mN/m at 20° C. and an osmolality of 312 mOsm/kg.

The nebulization was performed with an electronic vibrating membrane nebulizer (modified membrane nebulizer using the eFlow™ technology of PARI Pharma GmbH, Germany) having a large mixing chamber (with around 90 mL volume), an initial negative pressure in the liquid reservoir in the range of 100 to 400 mbar, and various membrane types having different hole sizes and hole geometries. The different membrane types are designed to generate different droplet or particle sizes (characterized by the mass median diameter (MMD) and geometric standard deviation (GSD)) and/or different output rates (e.g. drug delivery rate (DDR) or total output rate (TOR or so called output)). A normal output rate of a membrane placed in an aerosol generator device is defined below 0.55 mL/min and high output rate is defined by values of at least 0.55 mL/min. Alternatively the output rate can be characterized (or defined) in mg/min; then the normal output rate is e.g. below 550 mg/min and the high output rate is e.g. at least 550 mg/min. (Alternatively the limit for the high output rate may be defined by at least 0.50 mL/min, preferably at least 0.55 mL/min, more preferably at least 0.60 mL/min or most preferably at least 0.65 mL/min and the output rate in mg/min accordingly). The limit depends on the liquid characteristics, e.g. density, viscosity, surface tension and so on and may be defined for purposes of quality assurance of the aerosol generator devices, for example may be defined for a surrogate solution like sodium chloride 0.9% instead of the Ig, e.g. IgG, IgA and/or IgM solution. Then the normal output rate of the surrogate solution (e.g. sodium chloride 0.9%) generated from a membrane built in an aerosol generator device is defined by at least 0.55 mL/min, more preferably at least 0.60 mL/min and more preferred at least 0.65 mL/min. Alternatively the high output rate is at least 550 mg/min, preferred at least 600 mg/min and more preferred at least 650 mg/min. The membrane types that were used for nebulizing the IgG composition are identified and characterized in Table 1.

TABLE 1

Membrane types used for nebulizing IgG composition (using eFlow ™ technology)

| Membrane type | Nebulizer characteristics | |
|---|---|---|
| | MMD ranges | Output ranges |
| Type 1 | 2.8-3.9 μm | Normal |
| Type 2 | 3.3-4.4 μm | Normal |
| Type 3 | 3.8-5.0 μm | Normal |
| Type 4 | 3.8-5.0 μm | High |

A laser diffraction instrument (Malvern MasterSizer X™) was used to determine the droplet sizes (expressed in terms of the Mass Median Diameter (MMD)) and the droplet size distribution (expressed in terms of the Geometric Standard Deviation (GSD)) of the generated aerosols. A volume of 2 mL of IgG composition was filled in the nebulizer reservoir and the aerosol generated when operating the nebulizer was analyzed by directing the aerosol cloud through the laser beam of the MasterSizer X™ instrument using an aspiration flow of 20 L/min. The temperature and relative humidity during the measurements were 23° C. (±2° C.) and 50% (±5%), respectively. In the same experiment, the Total Output Rate (TOR) was evaluated. The measurement was performed twice for each membrane type (n=2). The results (mean values and standard deviations (SD)) are shown in Table 2.

TABLE 2

Results of laser diffraction experiments and Total Output Rate

| Membrane | MMD (μm) | | GSD | | TOR (mg/min) | |
|---|---|---|---|---|---|---|
| type | Mean | SD | Mean | SD | Mean | SD |
| Type 1 | 3.2 | 0.2 | 1.5 | 0.1 | 272 | 36.8 |
| Type 2 | 3.6 | 0.2 | 1.5 | 0.0 | 401 | 72.1 |
| Type 3 | 4.2 | 0.1 | 1.5 | 0.1 | 346 | 9.9 |
| Type 4 | 4.1 | 0.0 | 1.5 | 0.0 | 585 | 7.8 |

Example 2

Reproducibility of Nebulization of IgG

The laser diffraction experiments described in Example 1 were repeated with three modified membrane nebulizers using the eFlow™ technology and having a large mixing chamber (around 90 mL), an initial negative pressure in the liquid reservoir in the range of 100 to 400 mbar, using membranes of type 2 and type 4 (as specified above). In addition to determining MMD, GSD and TOR, the percentage of droplets smaller than 5 μm, smaller than 3.3 μm and smaller than 2 μm (i.e. the percentages of different Respirable Fractions (RF)) were measured. The fraction of droplets smaller than 5 μm gives a good indication of the percentage of droplets inhalable into the lower respiratory tract of an adult, whereas the fraction of droplets smaller than 3.3 μm provides an estimate of the percentage of droplets inhalable into the lower respiratory tract of a child. The fraction of droplets smaller than 2 μm indicates the percentage of droplets able to reach terminal bronchioles and alveoli. The lung deposition of aerosols with different particle size could be calculated by mathematical models, such as for example the ICRP model (The Respiratory Tract Deposition Model Proposed by the ICRP Task Group Radiat Prot Dosimetry (1991) 38(1-3): 159-165, A. C. James et al.), for different age groups, like adults, children, infants or babies.

The experiments were performed twice for each nebulizer tested (n=2). The results of the measurements are shown in Table 3.

TABLE 3

Results of laser diffraction experiments and Total Output Rate with different nebulizers

| Membrane type | Nebulizer (No. of measurements) | MMD (μm) | GSD | RF < 5 μm % | RF < 3.3 μm % | RF < 2 μm % | TOR (mg/min) |
|---|---|---|---|---|---|---|---|
| Type 2 | 1 (1) | 3.63 | 1.49 | 78.77 | 41.01 | 6.59 | 506 |
| | 2 (1) | 3.47 | 1.45 | 83.30 | 42.01 | 9.92 | 523 |
| | 3 (1) | 4.03 | 1.54 | 70.34 | 32.89 | 6.90 | 551 |
| | 1 (2) | 3.58 | 1.49 | 79.50 | 41.18 | 6.53 | 449 |
| | 2 (2) | 3.49 | 1.48 | 81.13 | 44.62 | 6.40 | 379 |
| | 3 (2) | 3.50 | 1.49 | 80.60 | 44.36 | 6.46 | 493 |
| Mean | | 3.6 | 1.5 | 78.9 | 41.0 | 7.1 | 484 |
| SD | | 0.2 | 0.0 | 4.5 | 4.3 | 1.4 | 61 |
| Type 4 | 1 (1) | 3.93 | 1.53 | 72.19 | 34.72 | 6.29 | 598 |
| | 2 (1) | 3.83 | 1.67 | 69.59 | 38.76 | 10.18 | 690 |
| | 3 (1) | 4.18 | 1.51 | 68.74 | 28.90 | 4.80 | 620 |
| | 1 (2) | 4.02 | 1.54 | 70.65 | 33.04 | 6.30 | 655 |
| | 2 (2) | 4.24 | 1.61 | 64.14 | 30.49 | 6.56 | 794 |
| | 3 (2) | 4.18 | 1.53 | 67.57 | 29.39 | 5.07 | 664 |
| Mean | | 4.1 | 1.6 | 68.8 | 32.6 | 6.5 | 670 |
| SD | | 0.2 | 0.1 | 2.8 | 3.8 | 1.9 | 69 |

Example 3

Nebulization of Various Immunoglobulin Formulations

Various plasma-derived immunoglobulin isotypes and polymers (IgA and IgM) as well as IgG formulations were nebulized and the aerosols obtained were characterized in a manner similar to that described in Example 1 using the same nebulizer and membranes.

More specifically, the characteristic of the aerosols obtained by nebulizing of the following formulations were compared by laser diffraction.

| No. | Description |
|---|---|
| 1 | 5%, monomeric IgA, in PBS (phosphate-buffered saline) |
| 2 | 5%, polymeric IgA + IgM, in PBS (called IGAM) |
| 3 | 10%, IgG in PBS (pH = 4.8) |
| 4 | 10%, IgG in glycine (0.25M, pH = 4.8) |
| 5 | 5%, IgG in proline |
| 6 | 10%, IgG in proline |
| 7 | 5%, monomeric IgA, in proline (called IgA) |
| 8 | 5%, polymeric IgA + IgM, in proline (called IgAM) |
| 9 | 5%, polymeric IgA + IgM associated with human recombinant secretory component, in proline (called SIgAM) |

The particle size distribution was determined by laser diffraction measurements (Malvern MasterSizer X™) of each of the formulations upon nebulization using an investigational eFlow™ nebulizer system with a large mixing chamber and a reservoir inducing negative pressure while closing each, with 2 different membrane types (as specified in Example 1). The fill volume was 2 mL in each case. The parameters measured were MMD, GSD, total output rate (TOR) and Respirable Fraction. TOR was determined by weighing the filled nebulizer before nebulization and after complete nebulization and calculated by dividing the weight difference by the nebulization time.

All determinations were done in triplicate. The results (mean values of three determinations and standard deviations (SD)) are shown in Table 4.

TABLE 4

Results of laser diffraction experiments and Total Output Rate for various immunoglobulin formulations

| Formulation No. | Membrane type | Value | MMD (μm) | GSD | RF < 5 μm % | RF < 3.3 μm % | RF < 2 μm % | TOR (mg/min) |
|---|---|---|---|---|---|---|---|---|
| 1 | 2 | Mean | 3.52 | 1.52 | 79.28 | 44.15 | 8.36 | 547 |
| | | SD | 0.09 | 0.04 | 3.06 | 1.97 | 1.43 | 76 |
| | 4 | Mean | 4.06 | 1.59 | 67.95 | 33.26 | 7.24 | 756 |
| | | SD | 0.02 | 0.01 | 0.52 | 0.09 | 0.65 | 45 |
| 2 | 2 | Mean | 3.39 | 1.47 | 83.27 | 47.28 | 7.13 | 436 |
| | | SD | 0.05 | 0.02 | 1.44 | 1.31 | 0.56 | 37 |
| | 4 | Mean | 4.01 | 1.61 | 68.29 | 34.49 | 7.96 | 684 |
| | | SD | 0.03 | 0.06 | 2.41 | 0.85 | 1.02 | 39 |
| 3 | 2 | Mean | 3.30 | 1.46 | 85.26 | 49.77 | 7.48 | 279 |
| | | SD | 0.06 | 0.01 | 1.40 | 2.03 | 0.78 | 13 |
| | 4 | Mean | 3.90 | 1.53 | 72.62 | 35.33 | 6.41 | 572 |
| | | SD | 0.11 | 0.03 | 3.48 | 1.99 | 0.31 | 30 |
| 4 | 2 | Mean | 3.38 | 1.46 | 84.27 | 47.54 | 6.84 | 289 |
| | | SD | 0.06 | 0.01 | 1.82 | 1.91 | 0.20 | 8 |
| | 4 | Mean | 3.99 | 1.56 | 70.11 | 34.08 | 7.13 | 568 |
| | | SD | 0.05 | 0.06 | 2.63 | 1.09 | 1.26 | 16 |
| 5 | 4 | Mean | 3.98 | 1.6 | 69.68 | ND | ND | 812 |
| | | SD | 0.09 | 0.02 | 2.23 | ND | ND | 132 |
| 6 | 4 | Mean | 3.74 | 1.53 | 76.87 | ND | ND | 602 |
| | | SD | 0.07 | 0.02 | 2.04 | ND | ND | 88 |
| 7 | 4 | Mean | 3.86 | 1.57 | 73.13 | ND | ND | 700 |
| | | SD | 0.1 | 0.03 | 2.97 | ND | ND | 90 |
| 8 | 4 | Mean | 3.73 | 1.55 | 76.46 | ND | ND | 681 |
| | | SD | 0.11 | 0.03 | 3.24 | ND | ND | 38 |
| 9 | 4 | Mean | 4.05 | 1.54 | 69.98 | ND | ND | 710 |
| | | SD | 0.11 | 0.04 | 3.33 | ND | ND | 68 |

ND: not determined

These results show that all tested formulations could be nebulized with good performance.

Example 4

Breath Simulation Experiments

The nebulization of the compositions described in Example 1 and Example 3 was also evaluated in breathing simulation experiments with three modified membrane nebulizers using the eFlow™ technology and having a large mixing chamber using membranes of type 2 and type 4 (as specified above). Each of the nebulizers was tested twice (n=2).

The breathing simulation experiments were conducted using an adult breathing pattern according to Ph. Eur. 2.9.44 (i.e. sinusoidal flow with a tidal volume of 500 mL, 15 breaths per minute and an inhalation:exhalation (I:E) ratio of 50:50). In each test, a nebulizer was connected to a sinus pump (PARI Compass II™ breath simulator). An inspiratory filter (polypropylene; 3M) was installed between the nebulizer including the mouth piece and the pump and fixed with rubber connectors. The nebulizer was filled with 2 mL of the composition described in Example 1 and nebulization was initiated and continued until aerosol production was no longer visible. The drug containing aerosol droplets were collected on the inhalation filter.

To determine the delivered dose, i.e. the amount of immunoglobulin collected on the filter during nebulization, the inhalation filter was removed from the filter casing with forceps and was put in a 50 mL plastic tube with a screw cap. Afterwards, the filter casing was rinsed with 40 mL buffer containing 0.9% saline and 0.5% SDS (sodium dodecyl sulphate, 98.5%) in purified water, and the rinsing fluid was subsequently added to the tube with the filter. The filter was extracted for 1 h while shaking on a rotator.

Additionally, the nebulizer was rinsed several times with 40 mL of the above described buffer and the rinsing solution was collected in a beaker for determining the amount of drug remaining in the reservoir (residue).

The solutions resulting from the filter extraction and from the rinsing of the nebulizer were analyzed using UV spectrophotometry. A sample of each of the solutions was diluted with buffer to achieve a concentration of approximately 0.5 mg/mL immunoglobulin. Approximately 0.8 mL of the diluted sample solution was filled in a disposable micro cuvette and measured against buffer at 280 nm. The Ig content in the solution was calculated according to the Beer-Lambert law (A=ε·c·L) using the mass absorption coefficient of ε(0.1%)=1.38 mL/(mg·cm). More specifically, the formula to calculate the Ig content is:

$$c\ (\text{mg/mL}) = \text{dilution factor} * A_{280} / \varepsilon * I$$

The respirable doses were calculated on the basis of the delivered dose and the mean respirable fractions determined by laser diffraction in Example 2.

During the breath simulation experiments, the nebulization time was also recorded. The results of the breath simulation experiments are summarized in Tables 5a and 5b. For each parameter tested, the mean of the results of 6 experiments per membrane type (i.e. 2 tests of 3 different nebulizers) is shown together with the standard deviation (SD).

TABLE 5a

Results obtained for IgG (10%) in breath simulation experiments

| | | Membrane type 2 | | Membrane type 4 | |
|---|---|---|---|---|---|
| | | Mean | SD | Mean | SD |
| Delivered Dose (DD) | mg | 112.20 | 13.27 | 108.50 | 11.72 |
| Delivered Dose (DD) | % | 54.42 | 6.45 | 52.61 | 5.76 |
| Residue in reservoir | % | 18.06 | 6.48 | 23.45 | 4.93 |
| Aerosol Losses (calculated) (due to exhalation) | % | 27.52 | 4.92 | 23.94 | 2.37 |
| Respirable Dose (RD) <5 μm | mg | 88.64 | 12.53 | 74.68 | 8.93 |
| Respirable Dose <5 μm | % | 42.99 | 6.09 | 36.21 | 4.39 |
| Respirable Dose <3.3 μm | mg | 46.01 | 7.47 | 35.51 | 7.20 |
| Respirable Dose <3.3 μm | % | 22.31 | 3.63 | 17.22 | 3.52 |
| Respirable Dose <2 μm | mg | 8.07 | 2.24 | 7.19 | 2.78 |
| Respirable Dose <2 μm | % | 3.91 | 1.09 | 3.49 | 1.35 |
| Nebulization time | min | 4.59 | 1.64 | 3.19 | 1.17 |

TABLE 5b

Results obtained for different formulations in breath simulation experiments

| Formulation | | 5 | 6 | 7 | 8 | 9 |
|---|---|---|---|---|---|---|
| DD | mg | 49.36 | 94.06 | 48.41 | 50.92 | 47.61 |
| SD | | 7.37 | 18.14 | 6.73 | 6.32 | 8.01 |
| DD | % | 47.7 | 45.4 | 48.9 | 51.4 | 47.2 |
| SD | | 7.1 | 9.0 | 6.9 | 6.3 | 8.5 |
| Residue in reservoir | % | 33.0 | 32.7 | 30.4 | 30.8 | 28.3 |
| SD | | 9.1 | 8.1 | 6.9 | 6.0 | 9.2 |
| RD < 5 μm | mg | 34.36 | 72.24 | 35.33 | 38.96 | 33.17 |

TABLE 5b-continued

Results obtained for different formulations in breath simulation experiments

| Formulation | | 5 | 6 | 7 | 8 | 9 |
|---|---|---|---|---|---|---|
| SD | | 4.91 | 13.64 | 4.59 | 5.37 | 4.49 |
| RD < 5 μm | % | 33.21 | 34.91 | 35.69 | 39.34 | 32.88 |
| SD | | 4.74 | 6.78 | 4.63 | 5.29 | 4.75 |
| Nebulization time | min | 2.2 | 3.0 | 2.6 | 2.4 | 2.8 |
| SD | | 0.4 | 0.4 | 0.3 | 0.2 | 0.5 |

Example 5

Biochemical Properties of Immunoglobulins after Nebulization (Molecular Size Characterization)

The nebulized compositions obtained in Example 1 and Example 3 were characterized for structural integrity and multimerization of the immunoglobulins. To this end, (i) SDS-PAGE, (ii) size exclusion chromatography (SEC) and (iii) dynamic light scattering (DLS) analysis were performed on samples of the nebulized composition.

The nebulized samples were collected directly after the nebulization process as follows: A Falcon tube was connected directly to the outlet of the nebulizer mixing chamber with elastomeric connectors. The nebulizers, connectors and the Falcon tubes were autoclaved before the experiments and the nebulization was conducted under laminar airflow conditions. The reservoir of the nebulizer was filled with 4 mL of sample formulation. The sampling tube was closed with a screw cap and frozen at −18° C. before integrity testing.

In total, 36 samples were subjected to SDS-PAGE and SEC analysis:

- 8 for IgG formulated with proline (FIG. 3): 2 non-nebulized control samples (a), 3 nebulized samples obtained with membrane type 2 (b) and 3 nebulized samples obtained with membrane type 4 (c). Samples were analyzed in duplicates (non-nebulized samples) and triplicates (nebulized samples), respectively.
- 14 for IgG in PBS (d, f, g) and in glycine (e, h, i) (FIG. 4): 2 non-nebulized controls (d, e), 6 nebulized samples obtained with membrane type 2 (f, h) and 6 nebulized samples obtained with membrane type 4 (g, i)). Samples were analyzed in triplicates (nebulized samples).
- 14 for IgA (j, l, m) and IgAM (k, n, o)(FIG. 4): 2 non-nebulized controls (j, k), 6 nebulized samples obtained with membrane type 2 (I, n) and 6 nebulized samples obtained with membrane type 4 (m, o)). Samples were analyzed in triplicates (nebulized samples).
- 10 for IgA (p,q), IgAM (r, s), SIgAM (t, u) and IgG (v, w, x, y) (FIG. 4): 5 non-nebulized controls (p, r, t, v, x) und 5 nebulized samples (q, s, u, w, y) obtained with membrane type 4.

All immunoglobulin solutions were prepared from the plasma of human blood donors. The IgG solutions had a protein concentration of 100 mg/mL and contained at least 98% of IgG. All three IgG formulations (250 mM proline; 250 mM glycine; PBS) had a pH of 4.8. The IgA solution and the IgAM (polymeric IgA+IgM) solution had a protein concentration of 50 mg/mL and were formulated in PBS with pH 7.4. The relative IgM content of the IgA solution was 2%, of the IgAM solution 35%. The IgA and IgAM solutions were also formulated in proline (125 mM). Human recombinant secretory component is associated to IgA and IgM in PBS and then formulated in proline (125 mM). IgM content in proline formulated IgA solutions were as follows: IgA (<2%), IgAM (33%), SIgAM (32%).

SDS-PAGE was carried out using the Mini-Cell system of Life Technologies, according to the manufacturer's protocols. Briefly, samples were denatured in sample buffer under reducing or non-reducing conditions, respectively, and electrophoretically separated on pre-cast gradient gels, NuPAGE Novex™ Bis-Tris 4-12% 1.0 mm 15 well, using NuPAGE™ MES electrophoresis buffer (Life Technologies). After electrophoresis, proteins in the gels were fixed and stained with Coomassie G-250 (SimplyBlue Safestain™; Life Technologies) according to the manufacturer's protocol. The protein staining pattern was digitally recorded using an ImageQuant™ LAS 4000 system (GE Healthcare Life-sciences).

Figure 3:
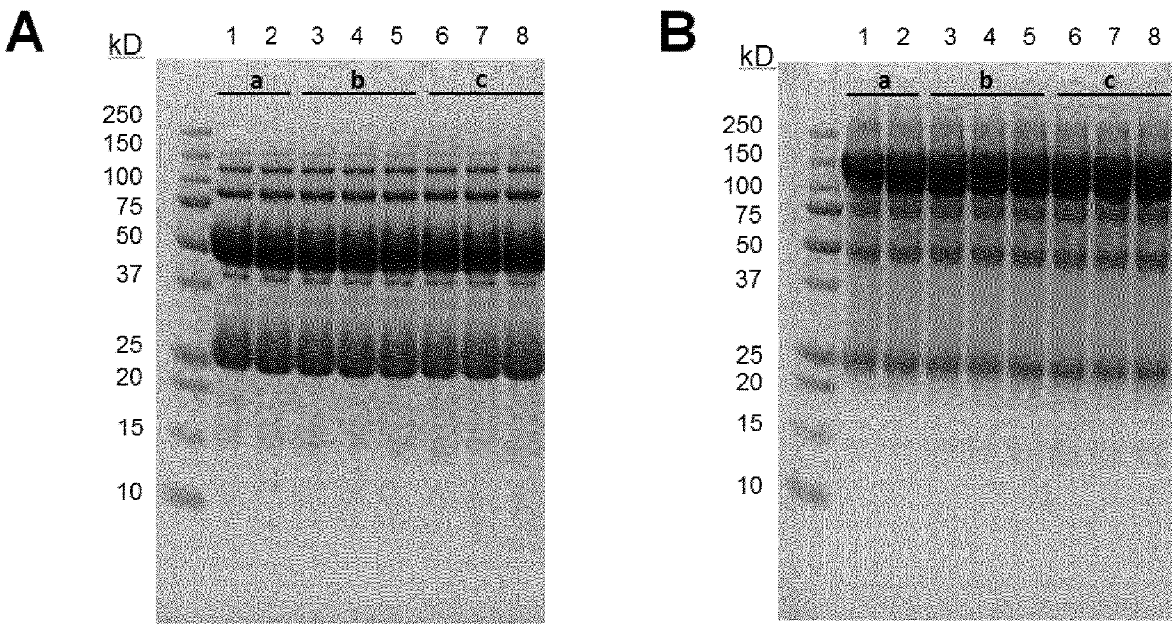
FIG. 3 shows the results of a structural analysis of non-nebulized and nebulized IgG composition (Privigen™) by SDS-PAGE under reducing (A) and non-reducing (B) conditions.
Figure 4:
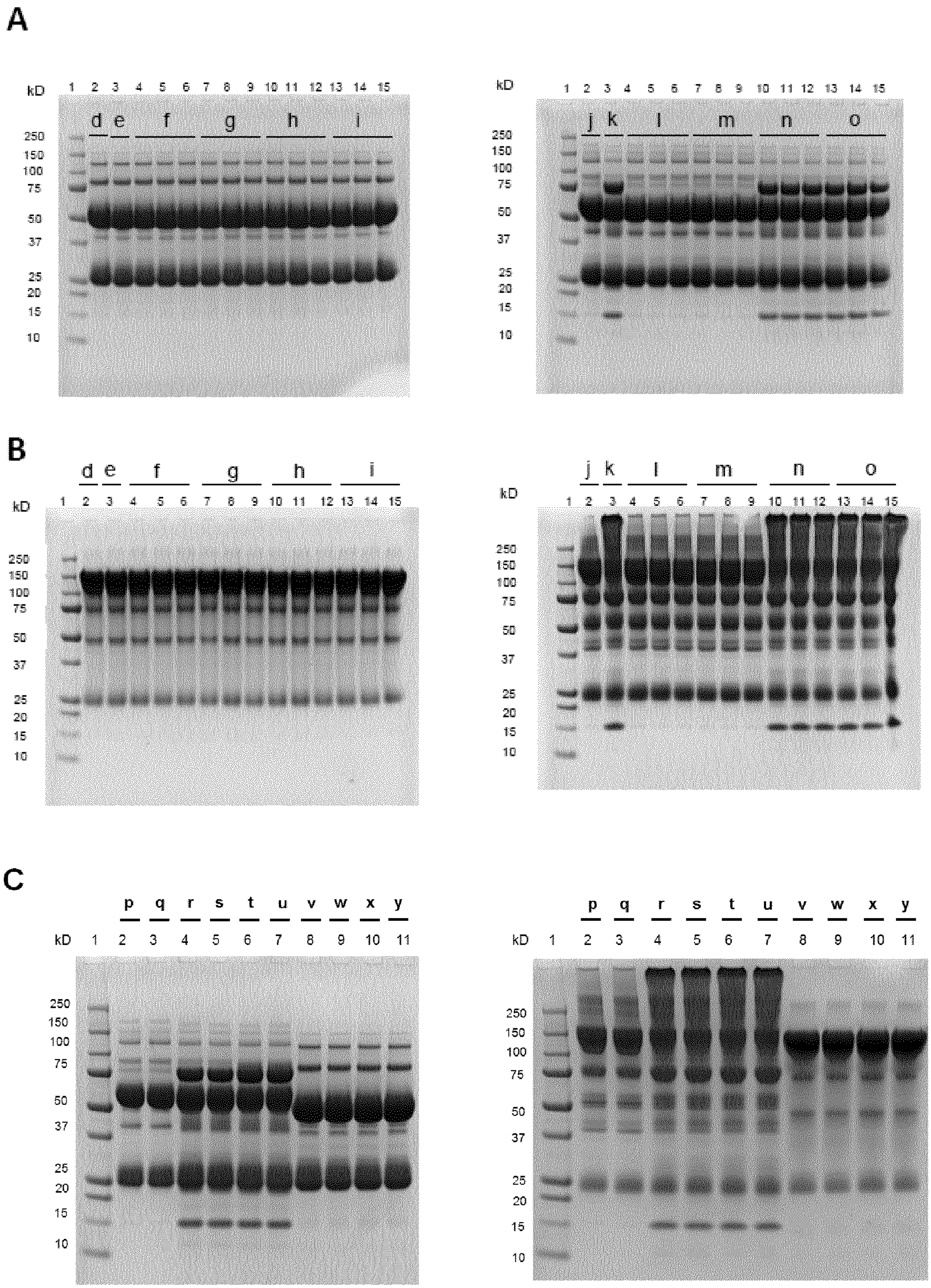
FIG. 4 shows the results of a structural analysis of non-nebulized and nebulized IgG (in PBS or glycine), IgA and IgAM compositions by SDS-PAGE under reducing (A) and non-reducing (B) conditions. (C) shows SDS-PAGE of further IgA (p, q), IgAM (r, s), SIgAM (t, u) and IgG (v, w, x, y) under reducing (left panel) and non-reducing (right panel) conditions.

The protein banding pattern obtained by SDS-PAGE analysis are shown in FIG. 3 (wherein the labels a, b and c refer to the aforementioned groups of samples) and in FIG. 4 (wherein the labels d, e, f, g, h, i, j, k, l, m, n, o, p, q, r, s, t, u, v, w, x and y refer to the aforementioned groups of samples). FIGS. 3A, 4A, 4C (left panel) show results obtained under reducing conditions and FIGS. 3B, 4B, 4C (right panel) show results obtained under non-reducing conditions.

For SEC analysis, samples were injected at 200 μg/2 μL (IgG) or 100 μg/2 μL (IgA, IgAM) into an Agilent Technologies 1260 Infinity™ HPLC system for size exclusion chromatography at a flow rate of 0.7 mL/min over a TSK gel G3000SWxl 7.8 mm ID×30 cm column (Tosoh Bioscience). From the resulting chromatograms the relative contents of (i) immunoglobulin polymers and aggregates, (ii) monomers and dimers, as well as (iii) fragments, respectively, were assessed. Results are shown in Tables 6 and 7.

For DLS analysis, samples were measured with a Malvern Zetasizer Nano™ in backscatter mode, with identical, fixed instrument settings for measurement position, detector attenuation, run duration, run number and measurement number, and the measurement results were averaged per sample with the proprietary Zetasizer software. Results are shown in Table 8.

TABLE 6

SEC analysis of nebulized IgG

| Formulation | Membrane type | | Aggregates (%) | Monomers and Dimers (%) | Frag-ments (%) |
|---|---|---|---|---|---|
| IgG, proline, 10% | non-nebulized control | | <1 | >98 | <1 |
| | Type 2 | Mean (n = 3) | <1 | >98 | <1 |
| | Type 4 | Mean (n = 3) | <1 | >98 | <1 |
| IgG, glycine-formulated | non-nebulized control | | <1 | >98 | <1 |
| | Type 2 | Mean (n = 3) | <1 | >98 | <1 |
| | Type 4 | Mean (n = 3) | <1 | >98 | <1 |

TABLE 6-continued

SEC analysis of nebulized IgG

| Formulation | Membrane type | | Aggregates (%) | Monomers and Dimers (%) | Frag-ments (%) |
|---|---|---|---|---|---|
| IgG in PBS, pH 4.8 | non-nebulized control | | 3 | >96 | <1 |
| | Type 2 | Mean (n = 3) | 4 | >95 | <1 |
| | Type 4 | Mean (n = 3) | 3 | >96 | <1 |
| IgG, proline, 5% | non-nebulized control | | <1 | >98 | <1 |
| | Type 4 | Mean (n = 3) | <1 | >98 | <1 |

TABLE 7

SEC analysis of nebulized IgA and IgAM

| Formulation | Membrane type | | Ig Polymers and Aggregates (%) | Monomers and Dimers (%) | Frag-ments (%) |
|---|---|---|---|---|---|
| IgA in PBS, pH 7.4 | non-nebulized control | | 17 | 80 | 3 |
| | Type 2 | Mean (n = 3) | 17 | 80 | 3 |
| | Type 4 | Mean (n = 3) | 16 | 81 | 3 |
| IgAM in PBS, pH 7.4 | non-nebulized control | | 56 | 39 | 5 |
| | Type 2 | Mean (n = 3) | 55 | 40 | 5 |
| | Type 4 | Mean (n = 3) | 55 | 40 | 5 |
| IgA, proline, 5% | non-nebulized control | | 21 | 75 | 4 |
| | Type 4 | Mean (n = 3) | 21 | 75 | 4 |
| IgAM, proline, 5% | non-nebulized control | | 54 | 40 | 6 |
| | Type 4 | Mean (n = 3) | 54 | 40 | 6 |
| SIgAM, proline, 5% | non-nebulized control | | 54 | 41 | 6 |
| | Type 4 | Mean (n = 3) | 56 | 39 | 5 |

TABLE 8

| DLS analysis of nebulized IgA/M | | | | | |
|---|---|---|---|---|---|
| Formulation | Membrane type | | Z-Average diameter (nm) | Polydispersity index | Mean Count Rate (kcps) |
| IgAM in PBS, pH 7.4 | non-nebulized control | | 36 | 0.40 | 297 |
| | Type 2 | Mean (n = 3) | 35 | 0.37 | 320 |
| | Type 4 | Mean (n = 3) | 35 | 0.35 | 322 |

Comparing non-nebulized and respective nebulized immunoglobulin samples, the protein banding pattern obtained by SDS-PAGE analysis was identical for all analyzed samples of the same immunoglobulin formulation (FIG. 3 and FIG. 4), both under reducing and non-reducing conditions, suggesting that the structural integrity of the immunoglobulin in the nebulized samples was preserved.

This finding is strongly supported by molecular size analysis using size exclusion high-performance liquid chromatography (SE-HPLC). The relative content of protein size categories (polymers & aggregates, monomers & dimers, and fragments) was comparable for all analyzed samples (Table 6, Table 7). Notably, an aggregate content of ≤1%, as observed with proline or glycine formulations of IgG, is very low for an aerosolized, highly concentrated IgG and even fulfills the requirement for intravenously administered IgG. Furthermore, immunoglobulin preparations with an increased content of high-molecular weight protein species, as the 10% (w/w) IgG formulated in acidified PBS (~3% of aggregate content), the 5% (w/w) IgA in PBS (~17% Ig polymers & aggregates), the 5% (w/w) IgA in proline (~21% Ig polymers & aggregates), the 5% (w/w) IgAM in PBS (~55% Ig polymers & aggregates), the 5% (w/w) IgAM in proline (~54% Ig polymers & aggregates) and the 5% (w/w) SIgAM in proline (~56% Ig polymers & aggregates) were also not noticeably altered by the nebulization process.

Because the SEC analysis did not discriminate between Ig polymers and aggregates, the polymer-rich IgAM samples before and after nebulization were further analyzed by dynamic light scattering (DLS), a method with increased sensitivity for larger particles. Alteration of the Ig protein particle size distribution due to the formation of protein aggregates would be revealed by DLS analysis. However, DLS results for Z-Average, polydispersity and particle count rate indicate that nebulization caused no change in particle size distribution (Table 8).

In summary, the above biochemical analyses show almost no difference between non-nebulized and nebulized samples.

Example 6

Activity of Immunoglobulins after Nebulization

Immunoglobulins display distinct functions which are directly dependent on their Fab (fragment antigen binding) and Fc (fragment crystallizable) fragments. While the Fab part is involved in antigen recognition, the Fc part can bind to specialized receptors and activate downstream molecular pathways. Importantly, it can also activate the complement.

6a

Fc Activity of Immunoglobulins after Nebulization

The compositions described in Example 1 and Example 3 were nebulized with a modified membrane nebulizer using the eFlow™ technology and having a large mixing chamber using membranes of type 2 and type 4 (as specified above) and the generated aerosols were collected. The collected solutions were used to determine the activity of the immunoglobulin after nebulization, which was compared with the activity of immunoglobulin in the composition before nebulization in order to evaluate the influence of the nebulization process on the activity of the immunoglobulins.

The activity was first determined by testing antigen recognition capacity and Fc function of nebulized immunoglobulin. In all human Ig preparations, xenoreactive antibodies are present. Adding xenoantigens (rabbit erythrocytes) to such a composition leads to immune complex formation. The resulting immune complex is added to human polymorphonuclear neutrophils (PMN) which are then activated by the recognition and binding of the Fc fragment of the IgG on their FcγRII and FcγRIIIγ receptors or of the Fc fragment of the IgA on CD89 (IgA receptor). Free oxygen radicals are then generated (respiratory burst), which are detected by chemiluminescence. The extent of cell activation is dependent on the integrity of the Fc portion of immunoglobulins and the amount bound to the erythrocytes. To obtain data that are solely dependent on the quality of the Fc portion of immunoglobulins, the amount of antibodies bound to the rabbit erythrocytes is measured by FACS, and the chemiluminescence and binding data are computed. Immunoglobulins with a Fc activity ≥50% display a normal Fc function. The results are presented in Tables 9a and 9b. In Table 9b, Fc activity is shown as a percentage of pre-nebulization activity, which is calculated as follows:

Fc activity (sample)=Ig bound at half maximum chemiluminescence pre-nebulization/Ig bound at half maximum chemiluminescence post-nebulization*100%

All pre-nebulization immunoglobulins have a Fc activity ≥50%.

TABLE 9a

| Mean data obtained in respiratory burst experiments (formulation 6) | | |
|---|---|---|
| Membrane type | | Fc activity (%) |
| non-nebulized control | | 97.0 |
| Type 2 | Mean (n = 3) | 93.7 |
| | SD | 1.5 |
| Type 4 | Mean (n = 3) | 92.3 |
| | SD | 2.5 |

TABLE 9b

| Mean data obtained for different formulations in respiratory burst experiments | | | |
|---|---|---|---|
| Membrane type | Formulation | | Fc activity (% of pre-nebulization activity) |
| Type 4 | 5 | Mean (n = 4) | 101 |
| | | SD | 7 |
| | 6 | Mean (n = 4) | 101 |
| | | SD | 14 |
| | 7 | Mean (n = 4) | 94 |
| | | SD | 5 |
| | 8 | Mean (n = 4) | 126 |
| | | SD | 31 |
| | 9 | Mean (n = 4) | 105 |
| | | SD | 17 |

Normal IgG displayed 97% of Fc activity on the neutrophils. Nebulized IgG showed an Fc activity very close to the IgG control (Fc activity>90%) whichever nebulizing membrane type was used. Thus nebulized IgG was able to recognize xenoantigens and to bind and activate PMN as well as non-nebulized IgG.

Comparison of Fc activities of the different proline formulations (IgG, IgA, IgAM and SIgAM) before and after nebulization shows no loss of function during the nebulization process (Tables 9a and 9b).

In a second assay, Fc function is assessed by measuring complement activation. Nebulized IgG and control IgG are adsorbed to polystyrene microspheres, forming a model of an immune complex. These coated microspheres are then incubated with human serum as a complement source. The resulting complement activation is quantified by measuring the deposition of activated C3 fragments to the microspheres by FACS. By computing these data with data on the actual amount of IgG bound to the microspheres, the integrity of the Fc-portion of IgG is assessed.

It was thus found that nebulization of IgG does not affect IgG capacity to activate complement.

6b

Antigen Recognition by Immunoglobulins after Nebulization

Further characterization of biological properties of immunoglobulins after nebulization involves the analysis by ELISA of antigen recognition such as EBV, CMV, FSME, HB, HAV, HSV, VZV, mumps, rubella and measles, and complement binding reaction and receptor binding tests. In particular, Respiratory syncytial virus (RSV) and Pneumococcus polysaccharide (PCP) antigen recognition is assessed for all formulations (5-9). ELISAs are performed accordingly to the manufacturer's protocols. Results are presented in Tables 10a and 10b. Anti-RSV and Anti-PCP antigen antibodies are detected in each formulation of polyclonal immunoglobulins. Importantly, RSV and PCP antigen recognition by the different formulations is not affected by nebulization.

TABLE 10a

| RSV antigen recognition by immunoglobulins before and after nebulization | | | | | | |
|---|---|---|---|---|---|---|
| | Detection Antibody | | | | | |
| | IgG [U/g] Nebulization | | IgA [U/g] Nebulization | | IgM [U/g] Nebulization | |
| Formulation | pre | after | pre | after | pre | after |
| 5 | 13948.7 ± 820.9 | 14634.5 ± 1858.3 | 11.5 ± 0.0 | 11.5 ± 0.0 | <0 | <0 |
| 6 | 14249 ± 473.0 | 15334.1 ± 1976.7 | 11.8 ± 0.4 | 11.5 ± 0.0 | <0 | <0 |
| 7 | 121.7 ± 0.4 | 122.7 ± 0.9 | 1062.4 ± 241.4 | 857.5 ± 98.5 | 4.9 ± 1.0 | 5.7 ± 1.2 |
| 8 | 133.1 ± 2.8 | 136.7 ± 0.0 | 1434.9 ± 79.9 | 867.2 ± 357.1 | 69.0 ± 28.5 | 69.2 ± 29.3 |
| 9 | 136.7 ± 1.2 | 137.6 ± 2.4 | 998.2 ± 115.7 | 1024.8 ± 136.8 | 66.8 ± 32.5 | 68.3 ± 25.4 |

TABLE 10b

| PCP antigen recognition by immunoglobulins before and after nebulization | | | | | | |
|---|---|---|---|---|---|---|
| | Detection Antibody | | | | | |
| | IgG [mg/g] Nebulization | | IgA [U/g] Nebulization | | IgM [U/g] Nebulization | |
| Formulation | pre | after | pre | after | pre | after |
| 5 | 4505.3 ± 158.2 | 5325.6 ± 397.4 | 678.6 ± 254.7 | 618.2 ± 291.4 | 644.8 ± 300.5 | 658.8 ± 308.2 |
| 6 | 5106.7 ± 822.9 | 5498.9 ± 575.7 | 726.1 ± 334.1 | 622.5 ± 309.7 | 650.9 ± 305.7 | 656.3 ± 308.2 |
| 7 | 751.7 ± 364.1 | 755.5 ± 361.1 | 19108.1 ± 909.6 | 18849.7 ± 134.1 | 919.4 ± 267.4 | 902.9 ± 355.2 |
| 8 | 675.5 ± 355.1 | 678.5 ± 354.8 | 49058.3 ± 2119.2 | 47397.8 ± 1187.6 | 15575.1 ± 518.3 | 15777 ± 209.2 |
| 9 | 671.8 ± 360.2 | 673.2 ± 348.0 | 41792.9 ± 1508.8 | 41015.9 ± 448.4 | 14614.8 ± 698.4 | 15115.8 ± 1123.4 |

Figure 5:
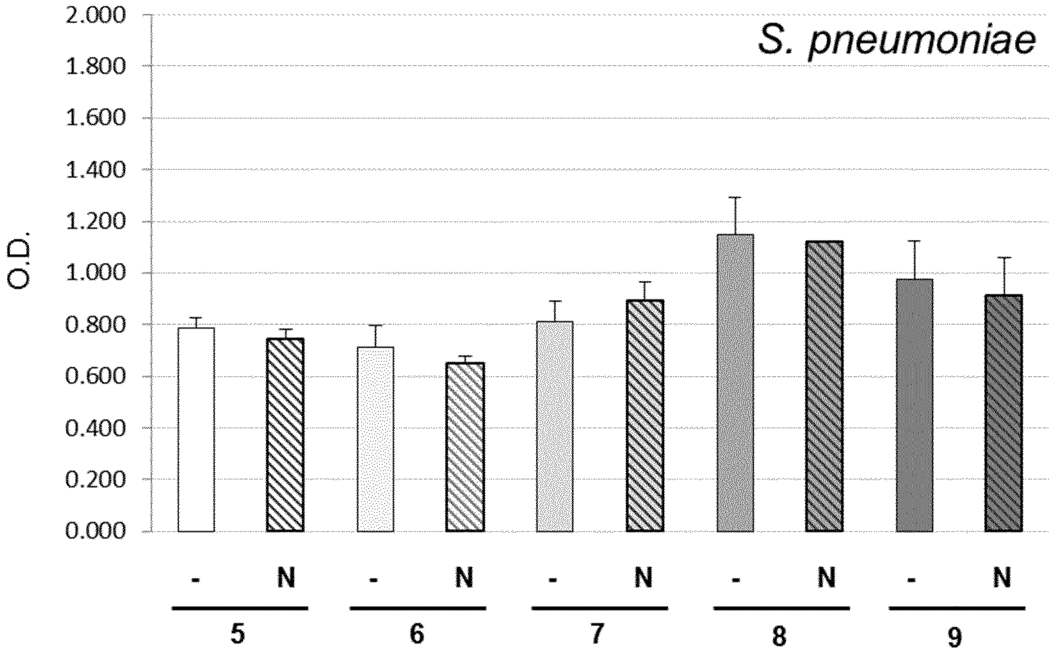
FIG. 5 shows the binding of different formulations to *S. pneumonia* before (−) and after (N) nebulization.

Antigen recognition was directly tested on bacteria. $5\times10^7$ CFU/mL of the *Streptococcus pneumoniae* A66.1 strain were coated onto polysorb plates (NUNC) in carbonate buffer at 4° C. overnight. After washing with PBS-Tween (0.05%), plates were blocked with 2.5% FCS (in PBS) for 1.5 h at room temperature. After washing with PBS-Tween (0.05%), formulations were added at 333 μg/mL (diluted in blocking buffer) and incubated for 2 h at room temperature. After washing with PBS-Tween (0.05%), secondary antibody (Goat anti Human IgG/NM-HRP (Novex); 1 mg/ml, 1:2,000 in blocking buffer) was incubated for 2 h at room temperature. Once washed with PBS-Tween (0.05%), TMB substrate was added to the wells and catalysis was stopped by adding HCL. Plates were then read in the plate reader. Results are presented in FIG. 5.

Anti-*S. pneumoniae* antibodies were detected in every formulation (5-9). IgAM and SIgAM showed a better titer of anti-*S. pneumoniae* antibodies, as depicted by the higher O.D. Importantly, comparison of nebulized formulations with the non-nebulized controls showed no difference in the recognition of the bacteria by the nebulized formulations. Therefore, nebulization did not affect bacterial antigen recognition by the polyclonal immunoglobulins.

6c

Activity of Nebulized Immunoglobulins in an In Vitro Infection Model

Figure 6:
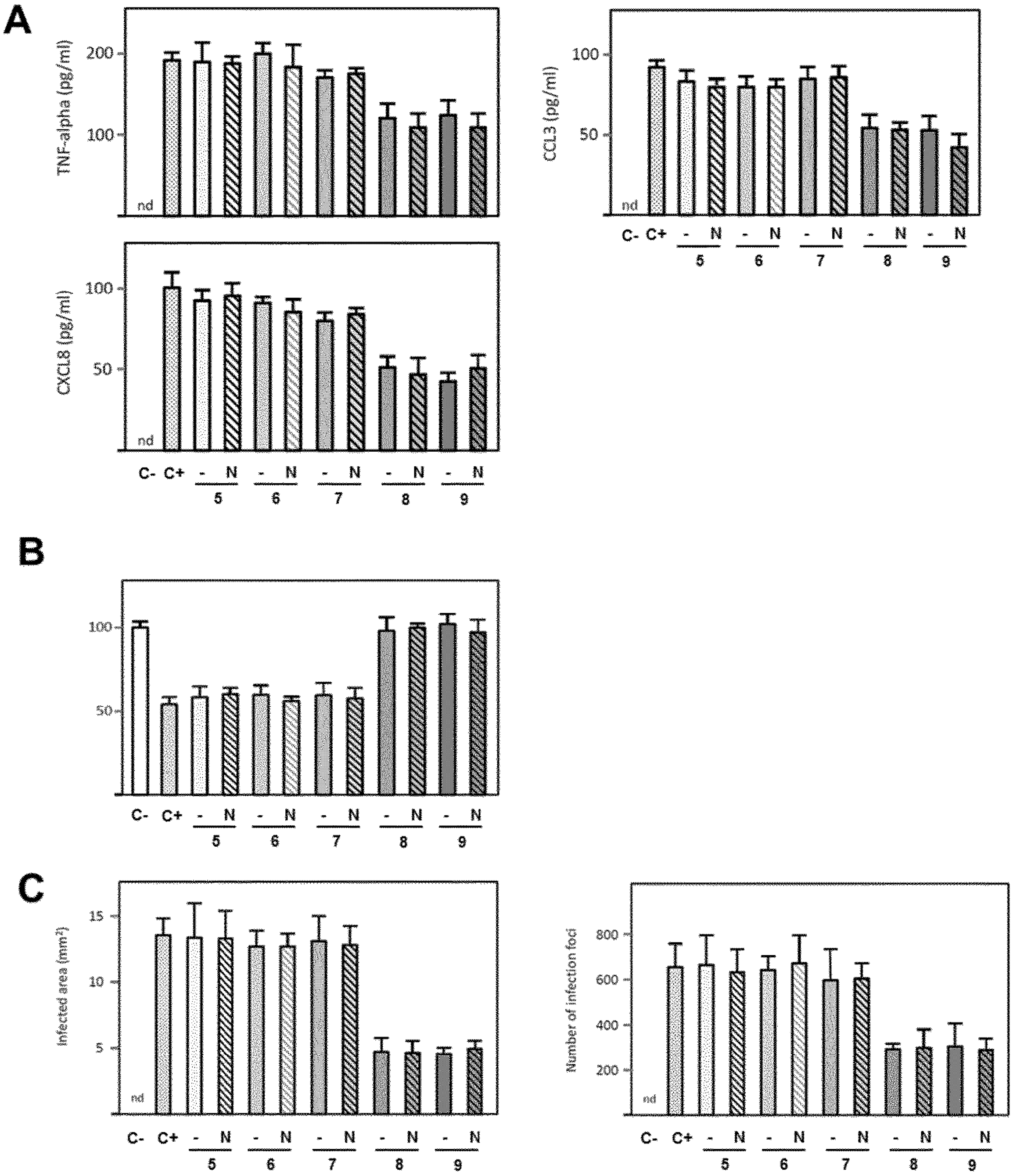
FIG. 6 shows the effect of nebulization on the activity of different formulations before and after nebulization on various aspects of *Shigella flexneri* infection of epithelial cell monolayers: (A) the effect on inflammatory cytokine secretion by epithelial cells in response to *Shigella flexneri* alone (C+), or in complex with unnebulized (−) or nebulized (N) formulation of the various immunoglobulin formulations; (B) effect of *Shigella flexneri* infection alone (C+), or in complex with unnebulized (−) or nebulized (N) formulations of the various immunoglobulin formulations on transepithelial membrane resistance of the cell monolayer; (C) infected area (left hand panel) and number of infection foci (right hand panel) after infection with *Shigella flexneri* alone (C+), or in complex with unnebulized (−) or nebulized (N) formulation of the various immunoglobulin formulations.

Polymeric immunoglobulins play an important role at mucosal surfaces. Immunoglobulins participate in preventing bacteria to enter the body, a process known as immune exclusion. It involves the recognition of antigens on the surface of bacteria by the immunoglobulins as well as the capacity of polymeric immunoglobulins to better aggregate bacteria, To assess if nebulization may harm functions of polymeric immunoglobulins, formulations (5-9) were tested in an in vitro model of infection of polarized mucosal epithelial cells. *Shigella flexneri* was used as infectious agent as it is known for infecting mucosal epithelial cells of the intestine, leading to diarrhea in human. Intestinal cell monolayer was used for this purpose. The cell monolayer was left untreated (C−) or exposed for 14 h to *Shigella flexneri* alone (C+) or in complex with control formulation (−) or nebulized formulations (N)(FIG. 6). Infection by *Shigella flexneri* induced the secretion of inflammatory cytokine by the epithelial cells, such as TNF-alpha, CXCL8 and CCL3 (FIG. 6A). In addition, infection led to a loss of membrane integrity and tight junctions which could be assessed by measuring the associated loss of transepithelial electrical resistance (FIG. 6B). At last, infection was monitored by counting the number of infected foci and measuring the infected area (FIG. 6C). Detailed protocols to measure these end-points are published in patent application WO2013132052, and in Longet S. et al, J Biol Chem. 2014 Aug. 1; 289(31):21617-26.

In such an in vitro model of infection, monomeric immunoglobulins are not protective (Longet S. et al, J Biol Chem. 2014 Aug. 1; 289(31):21617-26). Only IgAM and SIgAM in proline reduced infection, inflammatory cytokine secretion and protected membrane integrity (FIG. 6A, B, C; formulations 8 and 9). Importantly, immune complexes of *Shigella flexneri* with nebulized IgAM and SIgAM could reduce infectivity of *Shigella flexneri* and cytokine secretion as much as immune complexes formed by *Shigella flexneri* and non-nebulized IgAM and SIgAM.

Nebulization of monomeric immunoglobulins (FIG. 6, formulation 5-7) did not have influence on their activities in vitro. Indeed, no gain or loss of function was observed in this infection model.

Overall, it was thus found that nebulization of polyclonal immunoglobulins does not alter immunoglobulin antigen recognition and Fc function.

Example 7

Pulmonary Deposition of Nebulized Immunoglobulins in an Animal Model

The compositions described in Example 1 and in Example 3 were nebulized and administered to rats using a membrane nebulizer connected to a flow pass chamber where the aerosol is distributed to the animals.

At different times after aerosol application (0, 1 h, 6 h, 12 h and 24 h), rats were sacrificed. Left lobes of the lungs were used for bronchioalveolar lavages (BAL). To this purpose, the trachea was cannulated and the lung lavaged two times with sterile PBS (2×5 mL). The yield from each individual BAL was pooled and collected into a sterile plastic tube. BAL samples were centrifuged (at 1500×g for 10 min at approximately 4° C.) and the BAL supernatant was aliquoted into two sterile tubes (ca 5 mL each). The right lobes were isolated, fixed and prepared for histology using standard techniques. Ig distribution in the lungs is then assessed using immunohistochemistry methods with specific secondary antibodies on the paraffin sections. Specific parts of the lung are studied (for instance, respiratory bronchioles, alveolar ducts, alveolar sacs, and alveoli).

Presence of immunoglobulins in BAL was measured by ELISA. For IgA detection, plates (NUNC) were coated with a goat anti-human IgA (Bethyl Laboratories; 1/500 in coating buffer (1.59 g $Na_2CO_3$, 2.93 g $NaHCO_3$, 1 ml $H_2O$, pH 9.6)) for 1 h at room temperature. After washing with PBS-Tween, blocking solution (PBS, 1% BSA) was added to the well and incubated for 1 h at room temperature. Blocking buffer is washed with PBS-Tween and samples are distributed in the plates and incubated for 2 h at 37° C. After washing with PBS-Tween, goat anti-human IgA-HRP (Bethyl Laboratories; 1/8000 in dilution buffer (low cross buffer (Candor), 1% Casein)) was added to the wells for 1 h at room temperature. After washing with PBS-Tween, TMB substrate was added to the wells for 15 minutes at room temperature and catalysis was stopped by adding stop solution.

Figure 7:
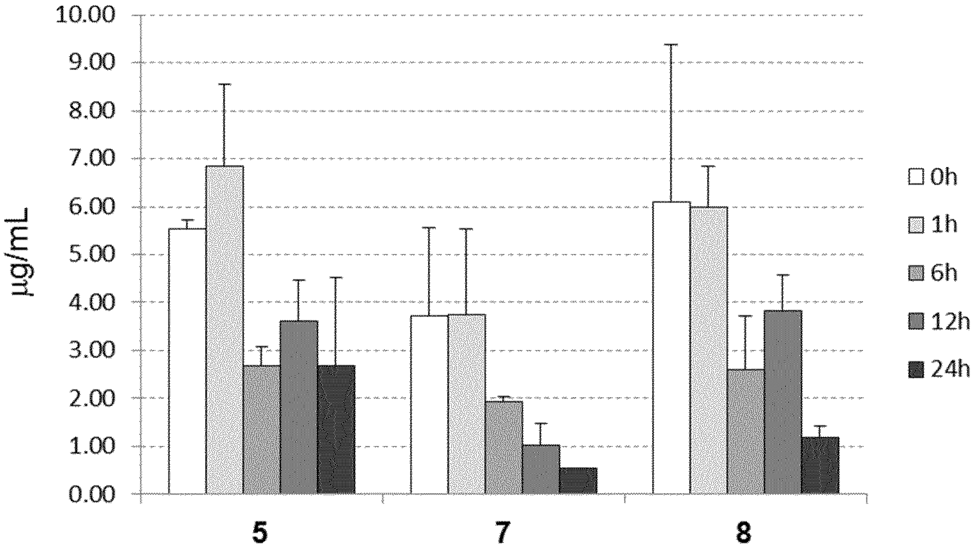
FIG. 7 shows the pulmonary deposition of nebulized immunoglobulin formulations, and the time course of their presence in BAL in an animal model.

For IgG detection, plates (NUNC) were coated with a goat anti-human IgG (Acris; final concentration of 1.5 μg/mL in coating buffer (1.59 g $Na_2CO_3$, 2.93 g $NaHCO_3$, 1 ml $H_2O$, pH 9.6)) for 2 h at room temperature. After washing with PBS-Tween, blocking solution (PBS, 1.6% BSA) was added to the well and incubated for 1 h at room temperature. Blocking buffer is washed with PBS-Tween and samples are distributed in the plates and incubated for 2 h at room temperature. After washing with PBS-Tween, goat anti-human IgG-HRP (Acris; final concentration of 0.3 μg/mL in dilution buffer (low cross buffer (Candor), 1% Casein)) was added to the wells for 1 h at room temperature. After washing with PBS-Tween, TMB substrate was added to the wells for 15 minutes at room temperature and catalysis was stopped by adding stop solution. Results are presented in FIG. 7.

The highest amount of immunoglobulins was detected in the BAL at the time of application of formulation 5, 7 and 8 by aerosol (time 0 h). Over time, the amount of nebulized immunoglobulins was decreasing, with a lower amount detected at the end of the kinetic (24 h). Importantly, nebulized immunoglobulins were still detectable in the BAL 24 h post-nebulization.

Presence of nebulized immunoglobulins in plasma from rats was also analyzed. None of IgA formulations (IgA and IgAM) were detectable in the plasma at 24 h post-nebulization. However, nebulized IgG could be detected in the plasma of 3 rats 24 h after they received the aerosol (see Table 11).

TABLE 11

Nebulized IgG was detected in plasma 24 h after immunoglobulin delivery
Plasma

| Formulation | Sample | IgG (mg/mL) |
|---|---|---|
| 5 | 1 | <0.50 |
| | 2 | <0.50 |
| | 3 | 0.59 |
| | 4 | <0.50 |
| | 5 | 0.52 |
| | 6 | 0.51 |

We have shown above that nebulization does not affect the structure of the immunoglobulins. However, muscus layers in the lungs are known to contain proteases which could affect integrity of applied immunoglobulins. In order to complement the ELISA results from the BAL, we analyzed the integrity of the nebulized immunoglobulins by SDS PAGE. SDS PAGE was performed following standard protocols or as described in patent application WO2013132052. For immunoblotting polyclonal rabbit antibodies were used: a) rabbit anti-human gamma chain (Dako, horseradish peroxidase (HRP)-conjugated; 1/10,000 dilution), b) rabbit anti-human alpha chain (Dako, horseradish peroxidase (HRP)-conjugated: 1/5,000 dilution); c) rabbit anti-human mu chain (Dako, horseradish peroxidase (HRP)-conjugated; 1/3,000 dilution). All incubations were performed in PBS containing 5% milk powder and 0.5% Tween at ambient temperature for 3 hours. After final washing with PBS-Tween, immunodetection on membranes was revealed by chemiluminescence and digitally recorded in an ImageQuant LAS 4000 system (GE Healthcare Lifesciences). Western blots from reduced gels are shown on FIG. 8.

Figure 8:
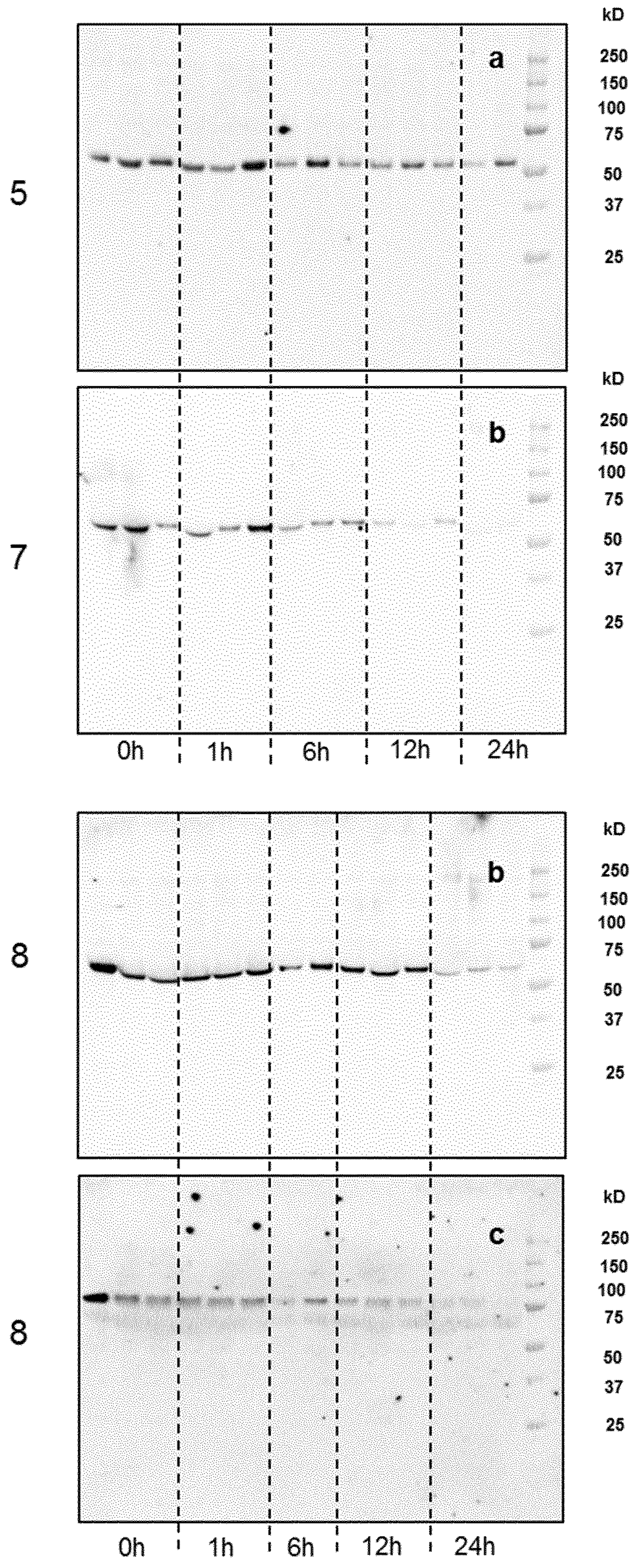
FIG. 8 shows Western blots of the BAL samples taken at time 0, 1 h, 6 h, 12 h and 24 h, probed with anti-gamma chain (a), anti-alpha chain (b), and anti-mu chain (c).

Corroborating ELISA data, gamma chain of IgG was detected in each BAL sample of rats having received nebulized IgG (FIG. 8; 5, a). Bands were detectable until 24 h post-nebulization. In BAL samples of rats which received nebulized IgA, alpha chain was detected (7, b) in early time points after delivery but fainted after 6 h. Alpha chain was indeed very hard to detect at 24 h post-nebulization (FIG. 8; 7, b). In rats which received nebulized IgAM, detection of alpha chain in each BAL sample was positive, with a lower signal at 24 h. In the same BAL samples, mu chain (c) was detected in each sample until 24 h, albeit faint at this last time point.

BAL samples were also run on non-reduced gels. No fragments of gamma, alpha and mu chains were detected. The immunoglobulins which were detected were intact.

Altogether, we have shown that nebulized immunoglobulins could efficiently reach the lungs of an animal and that these immunoglobulins stayed intact in this environment for 24 hours, even if their amount tended to reduce over time.

Example 8

Nebulized Immunoglobulins to Treat and Prevent of Chronic Sinusitis

Chronic sinusitis (CS) is one of the most frequent chronic infectious conditions (prevalence of 13% in immunodeficient patients and the normal population) causing significantly impaired quality of life (Khalid A N, Quraishi S A, Kennedy D W. Long-term quality of life measures after functional endoscopic sinus surgery. Am J Rhinol 2004 May; 18(3):131-6) and substantial health care consumption (Anand V K. Epidemiology and economic impact of rhinosinusitis. Ann Otol Rhinol Laryngol Suppl 2004 May; 193:3-5.).

Current treatments include antibiotics, long-term steroids and (repetitive) surgery. However, these interventions have limited efficacy with a high rate of failure in high-risk groups (e.g. primary antibody deficiency, cystic fibrosis) and antibiotic resistance could potentially develop from repetitive use.

To prevent or treat CS, the composition described in Example 1, preferably IgA or a mix of polymeric IgA and IgM optionally supplemented with recombinant secretory component, is nebulized and administered to targeted patients using a membrane nebulizer having a big mixing chamber and capable of emitting a pulsating air flow to target sinonasal or paranasal sinuses. Targeted patients are patients known for belonging to a high-risk group (e.g. primary antibody deficiency, cystic fibrosis) or for having recurrent episodes of CS.

In patients suffering from CS, application starts after surgical nasal polyp removal and/or antibiotic or steroid treatments. Patients nebulize 2 mL of a liquid composition including IgG (10%) or IgA (50 mg/mL) or a mix of polymeric IgA and IgM (50 mg/mL), preferably polymeric IgA and IgM (50 mg/mL) associated with recombinant secretory component, at least once a day for an 8-week period. This corresponds to one treatment cycle.

In a preventive therapy, patients nebulize 2 mL of a liquid composition including IgG (10%) or IgA (50 mg/mL) or a mix of polymeric IgA and IgM (50 mg/mL), preferably polymeric IgA and IgM (50 mg/mL) associated with recombinant secretory component, 2-treatment cycles per year.

Nebulized immunoglobulins decrease the chronicity of sinusitis episodes in the case of a prophylactic treatment.

When applied in patients with CS, nebulized immunoglobulins reduce symptoms such as nasal congestion and discharge, facial pressure or pain, swelling around the eyes, cheeks and nose.

Example 9

Nebulized Immunoglobulins in the Treatment of Chronic Lower Respiratory Tract Infections in Primary Immunodeficiency (PID)

IgG replacement therapy in PID patients efficiently reduces the rate of pneumonia and severe infections. However, these patients still experience 3-4 infections per year and per patient. This high rate of infection in combination with inflammation indicates that IgG therapy has a low impact on chronic side effects of infection, such as bronchiectasis, chronic diarrhea, autoimmunity, and lymphoproliferative disorders.

Pneumonia, bronchiectasis and septicemia under long-term IgG replacement therapy were associated with low IgM while there was a significantly increased rate of gastrointestinal infections with low IgA (Oksenhendler E, Gerard L, Fieschi C, et al. Infections in 252 patients with common variable immunodeficiency. Olin Infect Dis 2008 May 15; 46(10):1547-54; Gregersen S, Aalokken T M, Mynarek G, et al. Development of pulmonary abnormalities in patients with common variable immunodeficiency: associations with clinical and immunologic factors. Ann Allergy Asthma Immunol 2010 June; 104(6):503-10; Quinti I, Soresina A, Guerra A, et al. Effectiveness of immunoglobulin replacement therapy on clinical outcome in patients with primary antibody deficiencies: Results from a multicenter prospective cohort study. J Olin Immunol 2011 Mar. 2.), indicating again that IgA and/or IgM might be critical missing factors.

Patients with bronchiectasis are susceptible to infection with *Pseudomonas aeruginosa*. X-linked Agammaglobulinaemia (XLA) is a disorder affecting a sub-population of PID patients. It is characterized by a defect in the generation of mature B lymphocytes as well as specific antibodies and by a low concentration of immunoglobulins in the serum. These patients display chronic infections which might lead to bronchiectasis development.

A specific study population with chronic lower respiratory tract infections is XLA patients having experienced a first episode of lung infection with *P. aeruginosa*. The objective of the treatment would then be the prevention of recurrence of infection and long-term prevention of bronchiectasis. For this particular indication either an IgA or a mixed IgM/IgA product is considered. Patients nebulize 2 mL of a liquid composition including IgG (10%) or IgA (50 mg/mL) or a mix of polymeric IgA and IgM (50 mg/mL), preferably polymeric IgA and IgM (50 mg/mL) associated with recombinant secretory component, at least once a day, for an 8-week period (=one treatment cycle). Patients should receive 2-treatment cycles per year.

Efficacy parameters are well defined, including infection recurrence rate, rate of bronchiectasis development, microbial load/inflammatory parameters in induced sputum.

Example 10

Nebulization of Viscous Immunoglobulin Formulations

As shown in the previous examples, nebulization of the immunoglobulins using investigational modified eFlow technology is harming neither the immunoglobulin structure nor their functions. To allow for shorter nebulization times when targeting a specific amount of immunoglobulins to be delivered into the airways (upper and/or lower), higher concentrations of immunoglobulins are preferred. The high molecular weight of immunoglobulins (150 kD to 1040 kD) as well as a high concentration of molecules is known to both, separately or in association, affect viscosity of the formulation. Viscosity directly influences performance of the nebulization.

In order to better understand how viscosity is affecting nebulization performance, several formulations were tested on three distinct devices. The investigational eFlow nebulizer (modified membrane type 4), the Omron Micro Air U22 and the Aerogen Aeroneb®Go were used.

Formulations are depicted in table 12.

TABLE 12 characteristic of the tested formulations

| Ig | IgG | IgAM |
|---|---|---|
| Concentration | 5.0% | 5.0% |
| | 7.0% | 8.0% |
| | 9.0% | 9.0% |
| | 11.0% | |
| | 13.0% | |
| | 15.0% | |
| | 20.0% | |

The laser diffraction experiments were conducted as described in Example 1, 2 and 3. 3 investigational modified eFlow nebulizers (active vibrating membrane and negative pressure), 3 Omron Micro Air U22 (passive vibrating membrane), and 1 Aerogen Aeroneb®Go (active vibrating membrane) were used for this study, Samples were tested in duplicate (Aeroneb®Go) or in triplicates (investigational modified eFlow, Micro Air U22). Omron and Aerogen nebulizers were used according to the instruction manual of the respective manufacturers. All formulations were tested in randomized order. Results are presented in Tables 13 and 14.

TABLE 13

Results of nebulizations with IgG formulations

| NEBULIZER | | | PARI IM-eFlow | | | | Omron Micro Air U22 | | | | Aerogen Aeroneb ®Go | | | |
|---|---|---|---|---|---|---|---|---|---|---|---|---|---|---|
| | | Viscosity [mPa*s] | MMD [µm] | TOR [mg/min] | RF < 5 µm [%] | GSD | MMD [µm] | TOR [mg/min] | RF < 5 µm [%] | GSD | MMD [µm] | TOR [mg/min] | RF < 5 µm [%] | GSD |
| IgG 5% | mean | 1.75 | 3.89 | 631 | 71.82 | 1.6 | 6.13 | 352 | 36.19 | 1.75 | 3.53 | 251 | 75.28 | 1.75 |
| | SD | 0.01 | 0.18 | 66 | 5.86 | 0.07 | 0.1 | 206.5 | 1.6 | 0.1 | 0.1 | 23 | 2.9 | 0 |
| IgG 7% | mean | 2.15 | 3.85 | 557 | 72.19 | 1.61 | 6.84 | 160 | 30.77 | 1.78 | 3.58 | 117 | 74.55 | 1.77 |
| | SD | 0.01 | 0.05 | 9 | 1.76 | 0.04 | 0.5 | 62.4 | 3.7 | 0.5 | 0 | 9.2 | 0.4 | 0 |
| IgG 9% | mean | 2.65 | 3.69 | 608 | 76.57 | 1.57 | n.a. | n.a | n.a | n.a | 2.1 | 20 | 96.51 | 1.73 |
| | SD | 0.01 | 0.01 | 62 | 0.57 | 0.02 | | | | | 0.5 | 5.7 | 3.2 | 0.1 |
| IgG 11% | mean | 3.22 | 3.54 | 528 | 81.87 | 1.51 | n.a. | n.a | n.a | n.a | n.a. | n.a. | n.a. | n.a. |
| | SD | 0.01 | 0.12 | 4 | 3 | 0.02 | | | | | | | | |
| IgG 13% | mean | 4.28 | 2.94 | 290 | 90.98 | 1.51 | n.a. | n.a | n.a | n.a | n.a. | n.a | n.a | n.a |
| | SD | 0.03 | 0.46 | 180 | 6.77 | 0.06 | | | | | | | | |

TABLE 13-continued

Results of nebulizations with IgG formulations

| NEBULIZER | | | PARI IM-eFlow | | | | Omron Micro Air U22 | | | | Aerogen Aeroneb ®Go | | | |
|---|---|---|---|---|---|---|---|---|---|---|---|---|---|---|
| | | Viscos-ity [mPa*s] | MMD [μm] | TOR [mg/min] | RF < 5 μm [%] | GSD | MMD [μm] | TOR [mg/min] | RF < 5 μm [%] | GSD | MMD [μm] | TOR [mg/min] | RF < 5 μm [%] | GSD |
| IgG 15% | mean | 5.79 | 3.21 | 235 | 87.82 | 1.52 | n.a. | n.a | n.a | n.a | n.a. | n.a | n.a | n.a |
| | SD | 0.04 | n = 1 | n = 1 | n = 1 | n = 1 | | | | | | | | |
| IgG 20% | mean | 14.53 | 2.33 | 6 | 97.19 | 1.5 | n.a. | n.a | n.a | n.a | n.a. | n.a | n.a | n.a |
| | SD | 0.07 | n = 1 | n = 1 | n = 1 | n = 1 | | | | | | | | |

n.a.: not applicable;
MMD: Mass Median Dameter;
TOR: Total Output Rate;
RF: Respirable Fraction;
GSD: Geometric Standard Deviation;
IM-eFlow: investigational modified eFlow

TABLE 14

Results of nebulizations with IgAM formulations

| NEBULIZER | | | PARI IM-eFlow | | | | Omron Micro Air U22 | | | |
|---|---|---|---|---|---|---|---|---|---|---|
| | | Viscos-ity [mPa*s] | MMD [μm] | TOR [mg/min] | RF < 5 μm [%] | GSD | MMD [μm] | TOR [mg/min] | RF < 5 μm [%] | GSD |
| IgAM 5% | mean | 3.88 | 3.77 | 600 | 74.4 | 1.58 | n.a. | n.a | n.a | n.a |
| | SD | 0.01 | 0.06 | 43 | 1.77 | 0.02 | | | | |
| IgAM 8% | mean | 10.92 | 3.11 | 255 | 89.31 | 1.54 | n.a. | n.a | n.a | n.a |
| | SD | 0.05 | 0.08 | 73 | 5.65 | 0.08 | | | | |
| IgAM 9% | mean | 15.87 | 2.48 | 135 | 94.69 | 1.56 | n.a. | n.a | n.a | n.a |
| | SD | 0.13 | 0.98 | 132 | 5.9 | 0.12 | | | | |

n.a.: not applicable;
MMD: Mass Median Dameter;
TOR: Total Output Rate;
RF: Respirable Fraction;
GSD: Geometric Standard Deviation;
IM-eFlow: investigational modified eFlow As depicted in the Tables 13 and 14, increasing concentration of the same protein (e.g. monomeric polyclonal immunoglobulin) was associated with an increase of viscosity (1.75 to 14.52 mPa*s for IgG ranging from 5% to 20%, respectively). For bigger and more complex proteins such as polymeric immunoglobulins (IgA and IgM), viscosity increased faster than for monomeric immunoglobulins. 5% and 9% IgG showed a viscosity of 1.75 and 2.65 mPa*s respectively while a formulation of polymeric IgA and IgM at a concentration 5% and 9% showed a viscosity of 3.88 and 15.87 mPa*s. Increased viscosity was associated with a decrease of the total output rate (TOR). Droplet size decreased minimally while viscosity increased.

Nebulization of increasing concentrations of polyclonal IgG was feasible with the investigational modified eFlow nebulizer (IM-eFlow) until a concentration of 13%. For 15% IgG, 1 nebulizer out of 3 could nebulize IgG. 20% IgG could also be nebulized by 1 nebulizer out of 3, but will a very low TOR (6 mg/min). The Omron Micro Air U22 could not nebulize formulation with a concentration higher than 7% of IgG, and with a very low TOR (160 mg/min) and bigger droplet size (>6 μm; IM-eFlow<4 μm). The Aerogen Aeroneb®Go could nebulize formulations of 7% and 9%, but with a very low TOR (117 and 20 mg/min respectively). For IgG at 7% and 9%, eFlow nebulizers display high performance (e.g. TOR>550 mg/min).

Nebulization of IgA and IgM formulations (e.g. IgAM 5% and 8%) is feasible with the eFlow nebulizers and with a good performance. IgAM at 9% could be nebulized only once with a normal performance. The Omron Micro Air U22 was not able to nebulize these formulations containing polymeric polyclonal immunoglobulins. The Omron and Aerogen devices were not able to generate an aerosol from immunoglobulin formulations with a viscosity higher than 3 mPa*s.

Altogether, the present method of generating an aerosol by nebulizing a composition of polyclonal immunoglobulins shows a superior performance in nebulizing highly concentrated monomeric and polymeric immunoglobulins to the current method.

The invention claimed is:

1. A method for generating an aerosol comprising the steps:

(a) providing a liquid aqueous composition comprising a polyclonal immunoglobulin (Ig), wherein the Ig is a polyclonal immunoglobulin G (IgG), a polyclonal immunoglobulin A (IgA), and/or a polyclonal immunoglobulin M (IgM), and wherein the Ig has a concentration in a range of 40 to 200 mg per mL;

(b) providing a membrane nebulizer having a reservoir into which the liquid aqueous composition is filled; and (c) nebulizing the liquid aqueous composition using the membrane nebulizer to obtain the aerosol, wherein, prior to nebulization, the liquid aqueous composition has a viscosity of from 1 to 17 mPa·s.

2. The method of claim 1, wherein the concentration of the Ig is in a range of 40 to 100 mg per mL.

3. The method of claim 1, wherein the liquid aqueous composition further comprises a stabilizer.

4. The method of claim 3, wherein the stabilizer is proline.

5. The method of claim 1, wherein the liquid aqueous composition further comprises a surfactant.

6. The method of claim 1, wherein the reservoir is isolated from the atmosphere so that the pressure inside the reservoir decreases before or during step (c).

7. The method of claim 6, wherein the reservoir is isolated from the atmosphere by a sealing element (16) arranged on an opening in the reservoir (10) to provide a gas-tight seal for the opening, and a slidable element (21) is connected to the sealing element (16) in such a way that a movement of the slidable element (21) effects a movement of at least one section (18) of the sealing element (16) whereby a negative pressure is generated in the reservoir (10).

8. The method of claim 1, wherein the membrane nebulizer is a vibrating membrane nebulizer.

9. The method of claim 1, wherein the membrane nebulizer comprises a vibratable membrane (122) having a first side (124) in contact with the liquid aqueous composition and an opposite second side (125), the vibratable membrane having a plurality of holes (126) penetrating the membrane in an extension direction (E) from the first side to the second side, wherein the liquid aqueous composition passes through the holes from the first side to the second side when the vibratable membrane is vibrated to generate the aerosol at the second side, wherein each hole (126) has along its extension direction (E) a smallest diameter (Ds), a larger diameter (DO) that is up to three times larger than the smallest diameter, and a nozzle portion (132) bounded by the continuous portion of the hole in the extension direction comprising the smallest diameter of the hole and bordered by the larger diameter of the hole, and wherein the ratio of the total length of each hole (126) in the extension direction to the length of a respective the nozzle portions (132) in the extension direction is at least 4.

10. The method of claim 1, wherein the membrane nebulizer is adapted for generating an aerosol targeting the lower respiratory tract of a patient.

11. The method of claim 1, wherein the membrane nebulizer is adapted for generating an aerosol targeting the upper respiratory tract of a patient.

12. The method of claim 1, wherein the membrane nebulizer is an active membrane nebulizer.

13. The method of claim 1, wherein the aerosol contains at least 50% of the Ig initially in the liquid aqueous composition in the nebulizer reservoir.

14. The method of claim 1, wherein the activity of the Ig in the aerosol is at least 80% of the activity of the Ig initially in the liquid aqueous composition in the nebulizer reservoir.

15. The method of claim 1, wherein, prior to nebulization, the liquid aqueous composition has a viscosity of from 1 to 5 mPa·s.

* * * * *

UNITED STATES PATENT AND TRADEMARK OFFICE

CERTIFICATE OF CORRECTION

PATENT NO. : 11,471,617 B2
APPLICATION NO. : 15/300820
DATED : October 18, 2022
INVENTOR(S) : Cédric Pierre Vonarburg et al.

It is certified that error appears in the above-identified patent and that said Letters Patent is hereby corrected as shown below:

On the Title Page

Item (54) and in the Specification, Column 1, Line 1, Title, "Nebultzation" should read as --Nebulization--.

In the Claims

Claim 9, Column 38, Line 2, "(Ds)" should read as --($D_S$)--.

Claim 9, Column 38, Line 2, "(DO)" should read as --($D_L$)--.

Signed and Sealed this
Thirteenth Day of December, 2022

Katherine Kelly Vidal

Katherine Kelly Vidal
*Director of the United States Patent and Trademark Office*